United States Patent
Utley et al.

(10) Patent No.: US 7,959,627 B2
(45) Date of Patent: Jun. 14, 2011

(54) PRECISION ABLATING DEVICE

(75) Inventors: David S. Utley, Redwood City, CA (US); Robert Garabedian, Mountain View, CA (US); Michael P. Wallace, Pleasanton, CA (US)

(73) Assignee: BARRX Medical, Inc., Sunnyvale, CA (US)

( * ) Notice: Subject to any disclaimer, the term of this patent is extended or adjusted under 35 U.S.C. 154(b) by 0 days.

(21) Appl. No.: 11/286,257

(22) Filed: Nov. 23, 2005

(65) Prior Publication Data

US 2007/0135809 A1 Jun. 14, 2007

(51) Int. Cl.
*A61B 18/12* (2006.01)
(52) U.S. Cl. .................. 606/41; 606/42; 606/52
(58) Field of Classification Search ........... 606/41–52; 600/101
See application file for complete search history.

(56) References Cited

U.S. PATENT DOCUMENTS

| | | | |
|---|---|---|---|
| 552,832 A | 1/1896 | Fort | |
| 1,798,902 A | 3/1931 | Raney | |
| 3,517,128 A | 6/1970 | Hines | |
| 3,901,241 A | 8/1975 | Allen, Jr. | |
| 3,924,628 A | 12/1975 | Droegemueller et al. | |
| 4,011,872 A | 3/1977 | Komiya | |
| 4,196,724 A | 4/1980 | Wirt et al. | |
| 4,304,239 A | 12/1981 | Perlin | |
| 4,311,154 A | 1/1982 | Sterzer et al. | |
| 4,407,298 A | 10/1983 | Lentz et al. | |
| 4,411,266 A | 10/1983 | Cosman | |
| 4,423,812 A | 1/1984 | Sato | |
| 4,532,924 A | 8/1985 | Auth et al. | |
| 4,565,200 A | 1/1986 | Cosman | |
| 4,640,298 A | 2/1987 | Pless et al. | |
| 4,658,836 A | 4/1987 | Turner | |
| 4,662,383 A | 5/1987 | Sogawa et al. | |
| 4,674,481 A | 6/1987 | Boddie, Jr. et al. | |
| 4,676,258 A | 6/1987 | Inokuchi et al. | |
| 4,705,041 A | 11/1987 | Kim | |
| 4,709,698 A | 12/1987 | Johnston et al. | |
| 4,740,207 A | 4/1988 | Kreamer | |
| 4,765,331 A | 8/1988 | Petruzzi et al. | |
| 4,776,349 A | 10/1988 | Nashef et al. | |
| 4,823,791 A | 4/1989 | D'Amelio et al. | |
| 4,860,744 A | 8/1989 | Johnson et al. | |
| 4,887,614 A | 12/1989 | Shirakami et al. | |
| 4,895,138 A | 1/1990 | Yabe | |

(Continued)

FOREIGN PATENT DOCUMENTS

DE 3838840 5/1990

(Continued)

OTHER PUBLICATIONS

Salameh, Fadi M.D. 2004. An Animal Model Study to Clarify and Investigate Endoscopic Tissue Coagulation by Using a New Monopolar Device. 59 (1): 107-112.

(Continued)

*Primary Examiner* — Henry M Johnson, III
*Assistant Examiner* — Aaron Roane
(74) *Attorney, Agent, or Firm* — Shay Glenn LLP

(57) ABSTRACT

Apparatus for treating abnormal mucosa in an alimentary tract are provided. The apparatus include an ablation structure configured to be removably coupled to an endoscope and a deflection mechanism adapted to move the ablation structure with respect to the endoscope and toward a tissue surface.

28 Claims, 23 Drawing Sheets

U.S. PATENT DOCUMENTS

| | | | |
|---|---|---|---|
| 4,901,737 A | 2/1990 | Toone | |
| 4,906,203 A | 3/1990 | Margrave et al. | |
| 4,907,589 A | 3/1990 | Cosman | |
| 4,930,521 A | 6/1990 | Metzger et al. | |
| 4,943,290 A | 7/1990 | Rexroth et al. | |
| 4,947,842 A | 8/1990 | Marchosky et al. | |
| 4,949,147 A | 8/1990 | Bacuvier | |
| 4,955,377 A | 9/1990 | Lennox et al. | |
| 4,960,106 A | 10/1990 | Kubokawa et al. | |
| 4,966,597 A | 10/1990 | Cosman | |
| 4,969,890 A | 11/1990 | Sugita et al. | |
| 4,976,711 A | 12/1990 | Parins et al. | |
| 4,979,948 A | 12/1990 | Geddes et al. | |
| 4,998,539 A | 3/1991 | Delsanti | |
| 5,006,119 A | 4/1991 | Acker et al. | |
| 5,010,895 A | 4/1991 | Maurer et al. | |
| 5,019,075 A | 5/1991 | Spears et al. | |
| 5,035,696 A | 7/1991 | Rydell | |
| 5,045,056 A | 9/1991 | Behl | |
| 5,046,512 A | 9/1991 | Murchie | |
| 5,047,028 A | 9/1991 | Qian | |
| 5,056,532 A | 10/1991 | Hull et al. | |
| 5,057,107 A | 10/1991 | Parins et al. | |
| 5,078,717 A | 1/1992 | Parins et al. | |
| 5,083,565 A | 1/1992 | Parins | |
| 5,084,044 A | 1/1992 | Quint | |
| 5,088,979 A | 2/1992 | Filipi et al. | |
| 5,094,233 A | 3/1992 | Brennan | |
| 5,100,423 A | 3/1992 | Fearnot | |
| 5,106,360 A | 4/1992 | Ishiwara et al. | |
| 5,117,828 A | 6/1992 | Metzger et al. | |
| 5,122,137 A | 6/1992 | Lennox | |
| 5,125,928 A | 6/1992 | Parins et al. | |
| 5,151,100 A | 9/1992 | Abele et al. | |
| 5,156,151 A | 10/1992 | Imran | |
| 5,163,938 A * | 11/1992 | Kambara et al. | 606/47 |
| 5,171,299 A | 12/1992 | Heitzmann et al. | |
| 5,190,541 A | 3/1993 | Abele et al. | |
| 5,192,297 A | 3/1993 | Hull | |
| 5,197,963 A | 3/1993 | Parins | |
| 5,197,964 A | 3/1993 | Parins | |
| 5,205,287 A | 4/1993 | Erbel et al. | |
| 5,215,103 A | 6/1993 | Desai | |
| 5,232,444 A | 8/1993 | Just et al. | |
| 5,236,413 A | 8/1993 | Feiring | |
| 5,242,441 A | 9/1993 | Avitall | |
| 5,254,126 A | 10/1993 | Filipi et al. | |
| 5,255,679 A | 10/1993 | Imran | |
| 5,256,138 A | 10/1993 | Vurek et al. | |
| 5,257,451 A | 11/1993 | Edwards et al. | |
| 5,263,493 A | 11/1993 | Avitall | |
| 5,275,162 A | 1/1994 | Edwards et al. | |
| 5,275,169 A | 1/1994 | Afromowitz et al. | |
| 5,275,608 A | 1/1994 | Forman et al. | |
| 5,275,610 A | 1/1994 | Eberbach | |
| 5,277,201 A | 1/1994 | Stern | |
| 5,281,216 A | 1/1994 | Klicek | |
| 5,281,217 A | 1/1994 | Edwards et al. | |
| 5,281,218 A | 1/1994 | Imran | |
| 5,290,286 A | 3/1994 | Parins | |
| 5,292,321 A | 3/1994 | Lee | |
| 5,293,869 A | 3/1994 | Edwards et al. | |
| 5,305,696 A | 4/1994 | Mendenhall | |
| 5,309,910 A | 5/1994 | Edwards et al. | |
| 5,313,943 A | 5/1994 | Houser et al. | |
| 5,314,438 A | 5/1994 | Shturman | |
| 5,314,466 A | 5/1994 | Stern et al. | |
| 5,316,020 A | 5/1994 | Truffer | |
| 5,324,284 A | 6/1994 | Imran | |
| 5,328,467 A | 7/1994 | Edwards et al. | |
| 5,334,196 A | 8/1994 | Scott et al. | |
| 5,336,222 A | 8/1994 | Durgin, Jr. et al. | |
| 5,345,936 A | 9/1994 | Pomeranz et al. | |
| 5,348,554 A | 9/1994 | Imran et al. | |
| 5,363,861 A | 11/1994 | Edwards et al. | |
| 5,365,926 A | 11/1994 | Desai | |
| 5,365,945 A | 11/1994 | Halstrom | |
| 5,366,490 A | 11/1994 | Edwards et al. | |
| 5,368,557 A | 11/1994 | Nita et al. | |
| 5,368,592 A * | 11/1994 | Stern et al. | 606/33 |
| 5,370,675 A | 12/1994 | Edwards et al. | |
| 5,370,678 A | 12/1994 | Edwards et al. | |
| 5,372,138 A | 12/1994 | Crowley et al. | |
| 5,383,874 A | 1/1995 | Jackson et al. | |
| 5,383,876 A | 1/1995 | Nardella | |
| 5,383,917 A | 1/1995 | Desai et al. | |
| 5,385,544 A | 1/1995 | Edwards et al. | |
| 5,397,339 A | 3/1995 | Desai | |
| 5,398,683 A | 3/1995 | Edwards et al. | |
| 5,401,272 A | 3/1995 | Perkins | |
| 5,403,311 A | 4/1995 | Abele et al. | |
| 5,409,453 A | 4/1995 | Lundquist et al. | |
| 5,409,483 A | 4/1995 | Campbell et al. | |
| 5,411,025 A | 5/1995 | Webster, Jr. | |
| 5,413,573 A | 5/1995 | Koivukangas | |
| 5,415,657 A | 5/1995 | Taymor-Luia | |
| 5,421,819 A | 6/1995 | Edwards et al. | |
| 5,423,808 A | 6/1995 | Edwards et al. | |
| 5,423,811 A | 6/1995 | Ellman et al. | |
| 5,423,812 A | 6/1995 | Ellman et al. | |
| 5,425,704 A | 6/1995 | Sakurai et al. | |
| 5,428,658 A | 6/1995 | Oettinger et al. | |
| 5,433,739 A | 7/1995 | Sluijter et al. | |
| 5,435,805 A | 7/1995 | Edwards | |
| 5,441,499 A | 8/1995 | Fritzsch | |
| 5,443,470 A | 8/1995 | Stern et al. | |
| 5,454,782 A | 10/1995 | Perkins | |
| 5,454,809 A | 10/1995 | Janssen | |
| 5,456,662 A | 10/1995 | Edwards et al. | |
| 5,456,682 A | 10/1995 | Edwards et al. | |
| 5,458,571 A | 10/1995 | Lampropoulos et al. | |
| 5,458,596 A | 10/1995 | Lax et al. | |
| 5,458,597 A | 10/1995 | Edwards et al. | |
| 5,462,545 A | 10/1995 | Wang et al. | |
| 5,465,717 A | 11/1995 | Imran et al. | |
| 5,470,308 A | 11/1995 | Edwards et al. | |
| 5,471,982 A | 12/1995 | Edwards et al. | |
| 5,472,441 A | 12/1995 | Edwards et al. | |
| 5,484,400 A | 1/1996 | Edwards et al. | |
| 5,486,161 A | 1/1996 | Lax et al. | |
| 5,490,984 A | 2/1996 | Freed | |
| 5,496,271 A | 3/1996 | Burton et al. | |
| 5,496,311 A | 3/1996 | Abele et al. | |
| 5,500,012 A | 3/1996 | Brucker et al. | |
| 5,505,728 A | 4/1996 | Ellman et al. | |
| 5,505,730 A | 4/1996 | Edwards | |
| 5,507,743 A | 4/1996 | Edwards et al. | |
| 5,509,419 A | 4/1996 | Edwards et al. | |
| 5,514,130 A | 5/1996 | Baker | |
| 5,514,131 A | 5/1996 | Edwards et al. | |
| 5,517,989 A | 5/1996 | Frisbie et al. | |
| 5,520,684 A | 5/1996 | Imran | |
| 5,522,815 A | 6/1996 | Durgin, Jr. et al. | |
| 5,524,622 A | 6/1996 | Wilson | |
| 5,531,676 A | 7/1996 | Edwards et al. | |
| 5,531,677 A | 7/1996 | Lundquist et al. | |
| 5,533,958 A | 7/1996 | Wilk | |
| 5,536,240 A | 7/1996 | Edwards et al. | |
| 5,536,267 A | 7/1996 | Edwards et al. | |
| 5,540,655 A | 7/1996 | Edwards et al. | |
| 5,542,916 A | 8/1996 | Hirsch et al. | |
| 5,542,928 A | 8/1996 | Evans et al. | |
| 5,549,644 A | 8/1996 | Lundquist et al. | |
| 5,549,661 A | 8/1996 | Kordis et al. | |
| RE35,330 E | 9/1996 | Malone et al. | |
| 5,554,110 A | 9/1996 | Edwards et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,562,720 A | 10/1996 | Stern et al. | |
| 5,566,221 A | 10/1996 | Smith et al. | |
| 5,569,241 A | 10/1996 | Edwards | |
| 5,571,116 A | 11/1996 | Bolanos et al. | |
| 5,572,578 A | 11/1996 | Lin et al. | |
| 5,578,007 A | 11/1996 | Imran | |
| 5,588,432 A | 12/1996 | Crowley | |
| 5,588,960 A | 12/1996 | Edwards et al. | |

| | | | | | | |
|---|---|---|---|---|---|---|
| 5,591,195 A | 1/1997 | Taheri et al. | | 6,096,054 A | 8/2000 | Wyzgala et al. |
| 5,599,345 A | 2/1997 | Edwards et al. | | 6,102,908 A | 8/2000 | Tu et al. |
| 5,609,151 A | 3/1997 | Mulier et al. | | 6,112,123 A | 8/2000 | Kelleher et al. |
| 5,620,480 A | 4/1997 | Rudie | | 6,120,434 A * | 9/2000 | Kimura et al. ................ 600/114 |
| 5,621,780 A | 4/1997 | Smith et al. | | 6,123,703 A | 9/2000 | Tu et al. |
| 5,624,439 A | 4/1997 | Edwards et al. | | 6,123,718 A | 9/2000 | Tu et al. |
| 5,651,780 A | 7/1997 | Jackson et al. | | 6,138,046 A | 10/2000 | Dalton |
| 5,651,788 A | 7/1997 | Fleischer et al. | | 6,142,994 A | 11/2000 | Swanson et al. |
| 5,658,278 A | 8/1997 | Imran et al. | | 6,146,149 A | 11/2000 | Daoud |
| 5,672,153 A | 9/1997 | Lax et al. | | 6,162,237 A | 12/2000 | Chan |
| 5,676,674 A | 10/1997 | Bolanos et al. | | 6,179,836 B1 | 1/2001 | Eggers et al. |
| 5,688,266 A | 11/1997 | Edwards et al. | | 6,182,666 B1 | 2/2001 | Dobak, III |
| 5,688,490 A | 11/1997 | Tournier et al. | | 6,183,468 B1 | 2/2001 | Swanson et al. |
| 5,702,438 A | 12/1997 | Avitall | | 6,197,022 B1 | 3/2001 | Baker |
| 5,709,224 A | 1/1998 | Behl et al. | | 6,237,355 B1 | 5/2001 | Li |
| 5,713,942 A | 2/1998 | Stern et al. | | 6,238,392 B1 | 5/2001 | Long |
| 5,716,410 A | 2/1998 | Wang et al. | | 6,245,065 B1 | 6/2001 | Panescu et al. |
| 5,720,293 A | 2/1998 | Quinn et al. | | 6,254,598 B1 | 7/2001 | Edwards et al. |
| 5,730,128 A | 3/1998 | Pomeranz et al. | | 6,258,087 B1 | 7/2001 | Edwards et al. |
| 5,732,698 A | 3/1998 | Swanson et al. | | 6,258,118 B1 | 7/2001 | Baum et al. |
| 5,738,096 A | 4/1998 | Ben-Haim | | 6,273,886 B1 | 8/2001 | Edwards et al. |
| 5,748,699 A | 5/1998 | Smith | | 6,321,121 B1 | 11/2001 | Zelickson et al. |
| 5,769,846 A | 6/1998 | Edwards et al. | | 6,325,798 B1 | 12/2001 | Edwards et al. |
| 5,769,880 A | 6/1998 | Truckai et al. | | 6,325,800 B1 | 12/2001 | Durgin et al. |
| 5,779,698 A | 7/1998 | Clayman et al. | | 6,338,726 B1 | 1/2002 | Edwards et al. |
| 5,797,835 A * | 8/1998 | Green ........................ 600/106 | | 6,355,031 B1 | 3/2002 | Edwards et al. |
| 5,797,903 A | 8/1998 | Swanson et al. | | 6,355,032 B1 | 3/2002 | Hovda et al. |
| 5,800,334 A | 9/1998 | Wilk | | 6,358,245 B1 | 3/2002 | Edwards et al. |
| 5,800,429 A | 9/1998 | Edwards | | 6,363,937 B1 | 4/2002 | Hovda et al. |
| 5,807,261 A | 9/1998 | Benaron et al. | | 6,383,181 B1 | 5/2002 | Johnston et al. |
| 5,820,629 A | 10/1998 | Cox | | 6,394,949 B1 * | 5/2002 | Crowley et al. ................ 600/127 |
| 5,823,197 A | 10/1998 | Edwards | | 6,402,744 B2 | 6/2002 | Edwards et al. |
| 5,823,955 A | 10/1998 | Kuck et al. | | 6,405,732 B1 | 6/2002 | Edwards et al. |
| 5,827,273 A | 10/1998 | Edwards | | 6,409,723 B1 | 6/2002 | Edwards |
| 5,830,129 A | 11/1998 | Baer et al. | | H2037 H * | 7/2002 | Yates et al. ..................... 606/51 |
| 5,830,213 A | 11/1998 | Panescu et al. | | 6,415,016 B1 | 7/2002 | Chornenky et al. |
| 5,833,688 A | 11/1998 | Sieben et al. | | 6,416,511 B1 | 7/2002 | Lesh et al. |
| 5,836,874 A | 11/1998 | Swanson et al. | | 6,423,058 B1 | 7/2002 | Edwards et al. |
| 5,842,984 A | 12/1998 | Avitall | | 6,425,877 B1 | 7/2002 | Edwards |
| 5,846,196 A | 12/1998 | Siekmeyer et al. | | 6,428,536 B2 | 8/2002 | Panescu et al. |
| 5,860,974 A | 1/1999 | Abele | | 6,432,104 B1 | 8/2002 | Durgin et al. |
| 5,861,036 A | 1/1999 | Godin | | 6,440,128 B1 | 8/2002 | Edwards et al. |
| 5,863,291 A | 1/1999 | Schaer | | 6,448,658 B2 | 9/2002 | Takata et al. |
| 5,868,785 A | 2/1999 | Tal et al. | | 6,451,014 B1 | 9/2002 | Wakikaido et al. |
| 5,871,483 A | 2/1999 | Jackson et al. | | 6,454,790 B1 | 9/2002 | Neuberger et al. |
| 5,876,340 A | 3/1999 | Tu et al. | | 6,464,697 B1 | 10/2002 | Edwards et al. |
| 5,888,743 A | 3/1999 | Das | | 6,468,272 B1 | 10/2002 | Koblish et al. |
| 5,891,134 A | 4/1999 | Goble et al. | | 6,514,249 B1 | 2/2003 | Maguire et al. |
| 5,895,355 A | 4/1999 | Schaer | | 6,535,768 B1 | 3/2003 | Baker et al. |
| 5,902,263 A | 5/1999 | Patterson et al. | | 6,544,226 B1 | 4/2003 | Gaiser et al. |
| 5,925,044 A | 7/1999 | Hofmann et al. | | 6,547,776 B1 | 4/2003 | Gaiser et al. |
| 5,938,694 A | 8/1999 | Jaraczewski et al. | | 6,547,787 B1 | 4/2003 | Altman et al. |
| 5,964,755 A | 10/1999 | Edwards | | 6,551,302 B1 | 4/2003 | Rosinko et al. |
| 5,976,129 A | 11/1999 | Desai | | 6,551,310 B1 | 4/2003 | Ganz et al. |
| 5,984,861 A | 11/1999 | Crowley | | 6,551,315 B2 | 4/2003 | Kortenbach et al. |
| 5,997,534 A | 12/1999 | Tu et al. | | 6,562,034 B2 | 5/2003 | Edwards et al. |
| 6,004,262 A | 12/1999 | Putz et al. | | 6,572,578 B1 | 6/2003 | Blanchard |
| 6,006,755 A | 12/1999 | Edwards | | 6,572,610 B2 | 6/2003 | Kovalcheck et al. |
| 6,010,511 A | 1/2000 | Murphy | | 6,572,639 B1 | 6/2003 | Ingle et al. |
| 6,012,457 A | 1/2000 | Lesh | | 6,589,238 B2 | 7/2003 | Edwards et al. |
| 6,016,437 A | 1/2000 | Tu et al. | | 6,613,047 B2 | 9/2003 | Edwards |
| 6,023,638 A | 2/2000 | Swanson et al. | | 6,641,581 B2 | 11/2003 | Muzzammel |
| 6,027,499 A | 2/2000 | Johnston et al. | | 6,663,626 B2 | 12/2003 | Truckai et al. |
| 6,033,397 A | 3/2000 | Laufer et al. | | 6,673,070 B2 | 1/2004 | Edwards et al. |
| 6,039,701 A | 3/2000 | Sliwa et al. | | 6,682,528 B2 * | 1/2004 | Frazier et al. .................... 606/51 |
| 6,041,260 A | 3/2000 | Stern et al. | | 6,689,130 B2 | 2/2004 | Arail et al. |
| 6,044,846 A | 4/2000 | Edwards | | 6,695,764 B2 | 2/2004 | Silverman et al. |
| 6,053,913 A | 4/2000 | Tu et al. | | 6,712,074 B2 | 3/2004 | Edwards et al. |
| 6,056,744 A | 5/2000 | Edwards | | 6,712,814 B2 | 3/2004 | Edwards et al. |
| 6,059,719 A * | 5/2000 | Yamamoto et al. ............ 600/127 | | 6,712,815 B2 | 3/2004 | Sampson et al. |
| 6,068,629 A | 5/2000 | Haissaguerre et al. | | 6,740,082 B2 | 5/2004 | Shadduck |
| 6,071,277 A | 6/2000 | Farley et al. | | 6,749,607 B2 | 6/2004 | Edwards et al. |
| 6,073,052 A | 6/2000 | Zelickson et al. | | 6,752,806 B2 | 6/2004 | Durgin et al. |
| 6,086,558 A | 7/2000 | Bower et al. | | 6,800,083 B2 | 10/2004 | Hiblar et al. |
| 6,086,583 A | 7/2000 | Ouchi | | 6,837,886 B2 | 1/2005 | Collins et al. |
| 6,091,993 A | 7/2000 | Bouchier et al. | | 6,846,312 B2 | 1/2005 | Edwards et al. |
| 6,091,995 A | 7/2000 | Ingle et al. | | 6,860,878 B2 | 3/2005 | Brock |
| 6,092,528 A | 7/2000 | Edwards | | 6,866,663 B2 | 3/2005 | Edwards et al. |
| 6,095,966 A | 8/2000 | Chornenky et al. | | 6,872,206 B2 | 3/2005 | Edwards et al. |

| Patent/Pub No. | Date | Name |
|---|---|---|
| 6,917,834 B2 | 7/2005 | Koblish et al. |
| 6,918,906 B2 | 7/2005 | Long |
| 6,923,808 B2 | 8/2005 | Taimisto |
| 6,929,642 B2 | 8/2005 | Xiao et al. |
| 6,953,469 B2 | 10/2005 | Ryan |
| 6,964,661 B2 | 11/2005 | Rioux et al. |
| 6,971,395 B2 | 12/2005 | Edwards et al. |
| 6,974,456 B2 | 12/2005 | Edwards et al. |
| 6,994,704 B2 | 2/2006 | Qin et al. |
| 7,056,320 B2 | 6/2006 | Utley et al. |
| 7,083,620 B2 | 8/2006 | Jahns et al. |
| 7,089,063 B2 | 8/2006 | Lesh et al. |
| 7,097,644 B2 * | 8/2006 | Long .............................. 606/41 |
| 7,122,031 B2 | 10/2006 | Edwards et al. |
| 7,125,407 B2 | 10/2006 | Edwards et al. |
| 7,160,294 B2 | 1/2007 | Croft |
| 7,165,551 B2 | 1/2007 | Edwards |
| 7,167,758 B2 | 1/2007 | Baker et al. |
| 7,179,257 B2 | 2/2007 | West et al. |
| 7,293,563 B2 | 11/2007 | Utley et al. |
| 7,326,207 B2 | 2/2008 | Edwards |
| 7,329,254 B2 | 2/2008 | West et al. |
| 7,347,860 B2 | 3/2008 | Ouchi |
| 7,425,212 B1 | 9/2008 | Danek et al. |
| 2001/0041887 A1 | 11/2001 | Crowley |
| 2002/0128650 A1 | 9/2002 | McClurken |
| 2002/0177847 A1 | 11/2002 | Long |
| 2002/0183739 A1 | 12/2002 | Long |
| 2003/0093117 A1 | 5/2003 | Saadat |
| 2003/0109837 A1 | 6/2003 | McBride-Sakal |
| 2003/0153905 A1 | 8/2003 | Edwards et al. |
| 2003/0158550 A1 | 8/2003 | Ganz et al. |
| 2003/0181900 A1 | 9/2003 | Long |
| 2003/0181905 A1 | 9/2003 | Long |
| 2003/0191512 A1 | 10/2003 | Laufer et al. |
| 2003/0216727 A1 | 11/2003 | Long |
| 2004/0073204 A1 | 4/2004 | Ryan et al. |
| 2004/0087936 A1 | 5/2004 | Stern et al. |
| 2004/0122452 A1 | 6/2004 | Deem et al. |
| 2004/0147916 A1 | 7/2004 | Baker |
| 2004/0153120 A1 | 8/2004 | Seifert et al. |
| 2004/0172016 A1 | 9/2004 | Bek et al. |
| 2004/0204708 A1 | 10/2004 | Edwards et al. |
| 2004/0215180 A1 | 10/2004 | Starkebaum et al. |
| 2004/0215235 A1 | 10/2004 | Jackson et al. |
| 2004/0215296 A1 | 10/2004 | Ganz et al. |
| 2004/0236316 A1 | 11/2004 | Danitz et al. |
| 2005/0010162 A1 | 1/2005 | Utley et al. |
| 2005/0033271 A1 | 2/2005 | Qin et al. |
| 2005/0070978 A1 | 3/2005 | Bek et al. |
| 2005/0090817 A1 | 4/2005 | Phan |
| 2005/0096713 A1 | 5/2005 | Starkebaum et al. |
| 2005/0107829 A1 | 5/2005 | Edwards et al. |
| 2005/0143727 A1 | 6/2005 | Koblish et al. |
| 2005/0149013 A1 | 7/2005 | Lee |
| 2005/0154386 A1 | 7/2005 | West et al. |
| 2005/0159743 A1 | 7/2005 | Edwards et al. |
| 2005/0171524 A1 | 8/2005 | Stern et al. |
| 2005/0187546 A1 | 8/2005 | Bek et al. |
| 2005/0215983 A1 | 9/2005 | Brock |
| 2005/0228286 A1 | 10/2005 | Messerly et al. |
| 2005/0245926 A1 | 11/2005 | Edwards et al. |
| 2005/0288664 A1 | 12/2005 | Ford et al. |
| 2006/0009758 A1 | 1/2006 | Edwards et al. |
| 2006/0015162 A1 | 1/2006 | Edwards et al. |
| 2006/0020276 A1 | 1/2006 | Saadat et al. |
| 2006/0041256 A1 | 2/2006 | Edwards et al. |
| 2006/0069303 A1 | 3/2006 | Couvillon |
| 2006/0086363 A1 | 4/2006 | Qin et al. |
| 2006/0247614 A1 | 11/2006 | Sampson et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0282071 A1 | 12/2006 | Utley et al. |
| 2007/0066973 A1 | 3/2007 | Stern et al. |
| 2007/0100333 A1 | 5/2007 | Jackson et al. |
| 2007/0118159 A1 | 5/2007 | Deem et al. |
| 2007/0167963 A1 | 7/2007 | Deem et al. |
| 2007/0219570 A1 | 9/2007 | Deem et al. |
| 2008/0097427 A1 | 4/2008 | Stern et al. |
| 2008/0319350 A1 | 12/2008 | Wallace et al. |
| 2009/0012512 A1 | 1/2009 | Utley et al. |
| 2009/0012513 A1 | 1/2009 | Utley et al. |
| 2009/0012518 A1 | 1/2009 | Utley et al. |
| 2010/0234840 A1 | 9/2010 | Jackson et al. |

FOREIGN PATENT DOCUMENTS

| | | |
|---|---|---|
| DE | 4303882 | 8/1994 |
| EP | 0 105 677 A1 | 4/1984 |
| EP | 0 115 420 A2 | 8/1984 |
| EP | 0139607 | 5/1985 |
| EP | 0 251 745 A1 | 1/1988 |
| EP | 0521595 A2 | 1/1993 |
| EP | 0608609 | 8/1994 |
| EP | 1323382 A1 | 7/2003 |
| WO | WO 91/01773 | 2/1991 |
| WO | WO 91/03207 A1 | 3/1991 |
| WO | WO 92/10142 | 6/1992 |
| WO | WO 93/08755 | 5/1993 |
| WO | WO 94/07446 A1 | 4/1994 |
| WO | WO 94/10925 | 5/1994 |
| WO | WO 94/21165 | 9/1994 |
| WO | WO 94/21178 | 9/1994 |
| WO | WO 94/22366 | 10/1994 |
| WO | WO 94/26178 | 11/1994 |
| WO | WO 95/18575 | 7/1995 |
| WO | WO 95/19142 | 7/1995 |
| WO | WO 95/25472 | 9/1995 |
| WO | WO 96/00042 | 1/1996 |
| WO | WO 96/16606 | 6/1996 |
| WO | WO 96/29946 | 10/1996 |
| WO | WO 97/04702 | 2/1997 |
| WO | WO 97/06857 | 2/1997 |
| WO | WO 97/32532 | 9/1997 |
| WO | WO 97/43971 | 11/1997 |
| WO | WO 98/12999 A2 | 4/1998 |
| WO | WO 98/14238 A1 | 4/1998 |
| WO | WO 98/18393 A1 | 5/1998 |
| WO | WO 99/03413 | 1/1999 |
| WO | WO 99/35987 A1 | 7/1999 |
| WO | WO 99/42046 A1 | 8/1999 |
| WO | WO 99/55245 A1 | 11/1999 |
| WO | WO 00/01313 A1 | 1/2000 |
| WO | WO 00/59393 A1 | 10/2000 |
| WO | WO 00/62699 A2 | 10/2000 |
| WO | WO 00/66017 A1 | 11/2000 |
| WO | WO 00/66021 A1 | 11/2000 |
| WO | WO 00/66052 A1 | 11/2000 |
| WO | WO 00/69376 A1 | 11/2000 |
| WO | WO 01/22897 A1 | 4/2001 |
| WO | WO 01/35846 A1 | 5/2001 |
| WO | WO 01/45550 A2 | 6/2001 |
| WO | WO 01/89440 | 11/2001 |
| WO | WO 02/096327 A2 | 12/2002 |
| WO | WO 03/015651 A1 | 2/2003 |
| WO | WO 03/070091 A1 | 8/2003 |
| WO | WO 2004/043280 A1 | 5/2004 |
| WO | WO 2007/001981 A2 | 1/2007 |
| WO | WO 2007/061984 A2 | 5/2007 |

OTHER PUBLICATIONS

Jackson, et al., U.S. Appl. No. 11/244,385 "Methods and Systems for Determining Physiologic Characteristics for Treatment of the Esophagus" filed on Oct. 4, 2005.

Utley, et al. U.S. Appl. No. 11/286,444 "Precision Ablating Method" filed on Nov. 23, 2005.

Wallace, et al. U.S. Appl. No. 11/275,244 "Auto-Aligning Ablating Device and Method of Use" filed on Dec. 20, 2005.

Shadduck, J. H. U.S. Appl. No. 11/469,816 entitled "Surgical Instruments and Techniques For Treating Gastro-Esophageal Reflux Disease," filed Sep. 1, 2006.

Castell, D.O. Gastroesophageal Reflux Disease: Current Strategies for Patient Management. Arch Fam Med. 1996; 5(4):221-227.

Dallamagne et al; Laparoscopic Nissen Fundoplication: Preliminary. Surgical Laparoscopy and Endoscopy. 1991; 1(3):138-143.

Hinder et al; The Technique of Laparoscopic Nissen Fundoplication. Surgical Laparoscopy and Endoscopy. 1992; 2(3):265-272.

Kaneko et al; Physiological Laryngeal Pacemaker. Trans Am Soc. Artif Intern Organs. 1985; XXXI:293-296.

Karlstrom et al; Ectopic Jejunal Pacemakers and Enterogastric Reflux Roux Gastrectomy: Effect of Intestinal Pacing. Surgery. 1989; 106(3):486-495.

Kelly, K.A. et al; Duodenal-Gastric Reflux and Slowed Gastric Emptying by Electrical Pacing of the Canine Duodenal Pacesetter Potential. Gastroenterology. 1977; 72(3):429-433.

Mugica, et al. Direct Diaphragm Stimulation. PACE. 1987; 10:252-256.

Mugica, et al., Preliminary Test of a Muscular Diaphragm Pacing System on Human Patients. Neurostimulation: An Overview, chapter 21. 1985; 263-279.

Reynolds, J.C. Influence of Pathophysiology, Severity, and Cost on the Medical Management of Gastroesophageal Reflux Disease. Am J. Health-Syst Phar. 1996; 53(22sul3):S5-S12.

Rice et al; Endoscopic Paranasal Sinus Surgery. Chapter 5, Functional Endoscopic Paranasal Sinus Surgery, The Technique of Messerklinger. Raven Press. 1988; 75-102.

Rice et al; Endoscopic Paranasal Sinus Surgery. Chapter 6, Total Endoscopic Sphenoethmoidectomy. The Technique of Wigand. Raven Press. 1988; 103-125.

Urshel, J.D. Complications of Antireflux Surgery. Am J. Surg. 1993; 166(1):68-70.

Wallace et al; U.S. Appl. No. 11/830,251 entitled "Cleaning Devices and Methods," filed Jul. 30, 2007.

Utley et al; U.S. Appl. No. 11/830,291 entitled "Cleaning Device and Methods," filed Jul. 30, 2007.

Kelly et al.; U.S. Appl. No. 12/114,628 entitled "Method and apparatus for gastrointestinal tract ablation for treatment of obesity," filed May 2, 2008.

DiabetesInControl.com, "How tummy surgery cures diabetes in a matter of days," (website accessed Jun. 6, 2007).

Ganz et al; U.S. Appl. No. 12/259,136 entitled "System and method of treating abnormal tissue in the human esophagus," filed Oct. 27, 2008.

Utley, David S.; U.S. Appl. No. 12/270,373 entitled "System and method for ablational treatment of uterine cervical neoplasma," filed Nov. 13, 2008.

Shadduck, John; U.S. Appl. No. 12/368,943 entitled "Surgical instruments and techniques for treating gastro-esophageal reflux disease," filed Feb. 10, 2009.

Wallace et al.; U.S. Appl. No. 12/404,159 entitled "Auto-aligning ablating device and method of use," filed Mar. 13, 2009.

Utley et al.; U.S. Appl. No. 12/620,924 entitled "System for tissue ablation," filed Nov. 18, 2009.

Shadduck, John H.; U.S. Appl. No. 12/751,803 entitled "Surgical instruments and techniques for treating gastro-esophageal reflux disease," filed Mar. 31, 2010.

* cited by examiner

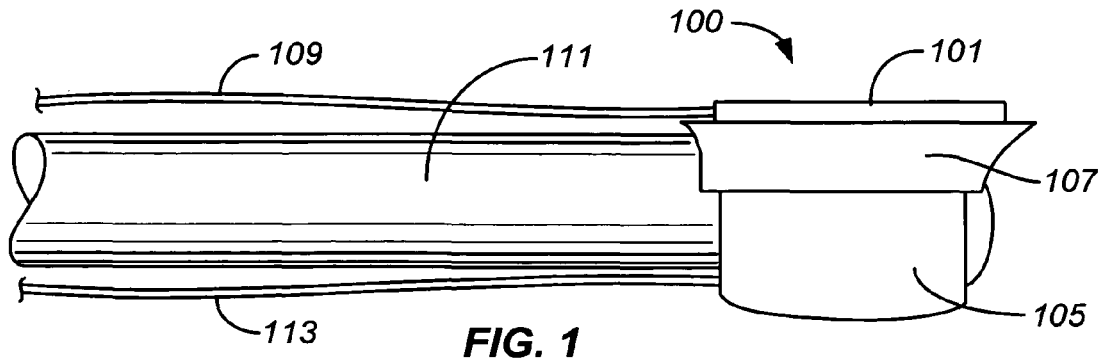
FIG. 1
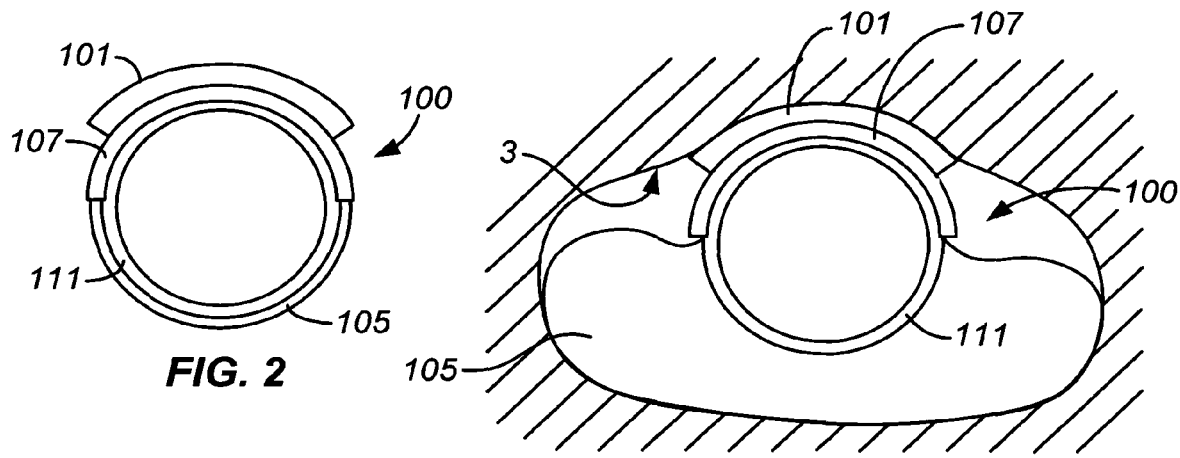
FIG. 2  FIG. 3
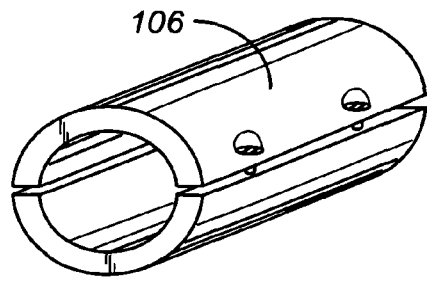
FIG. 4
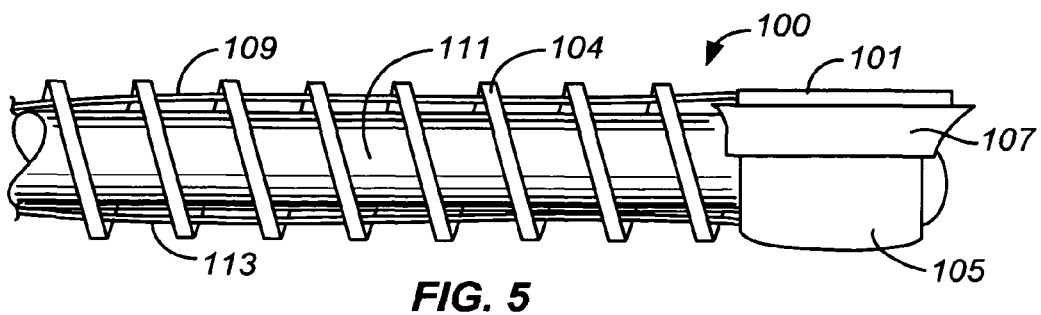
FIG. 5

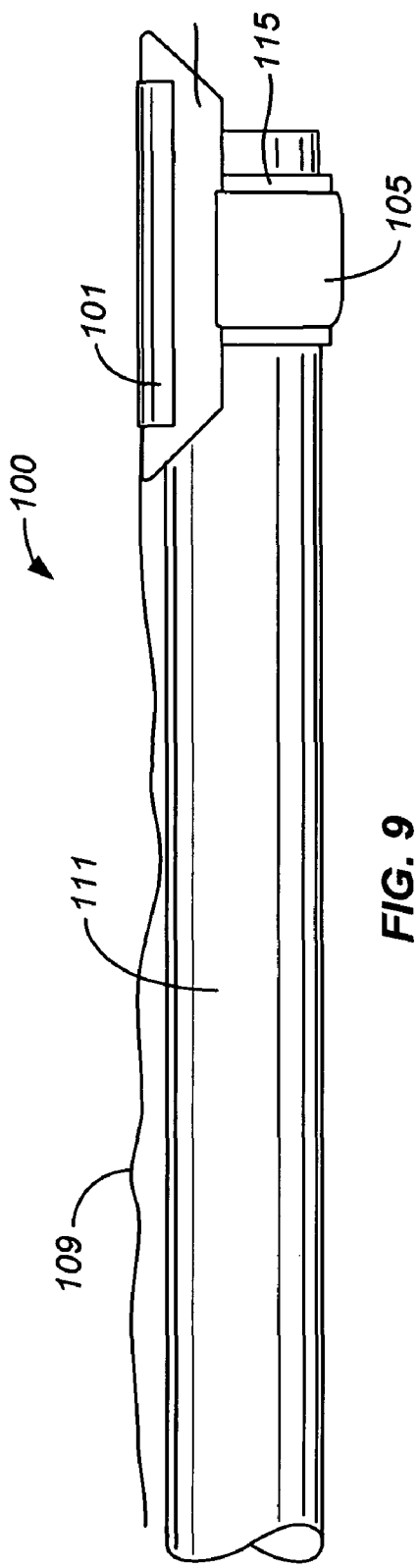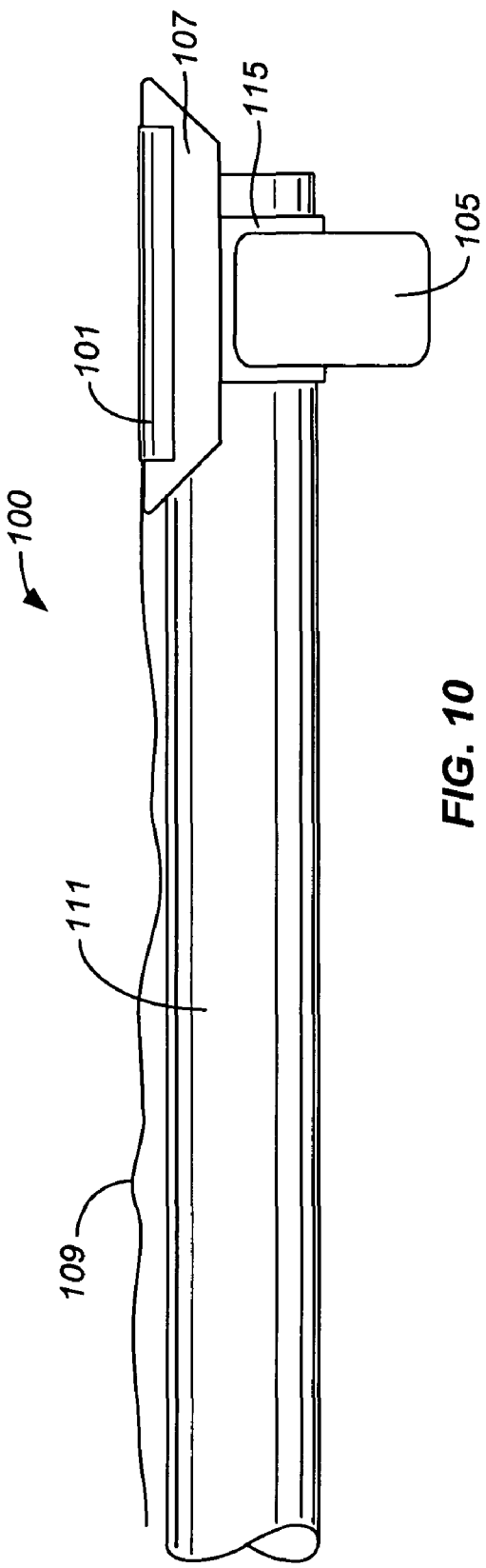

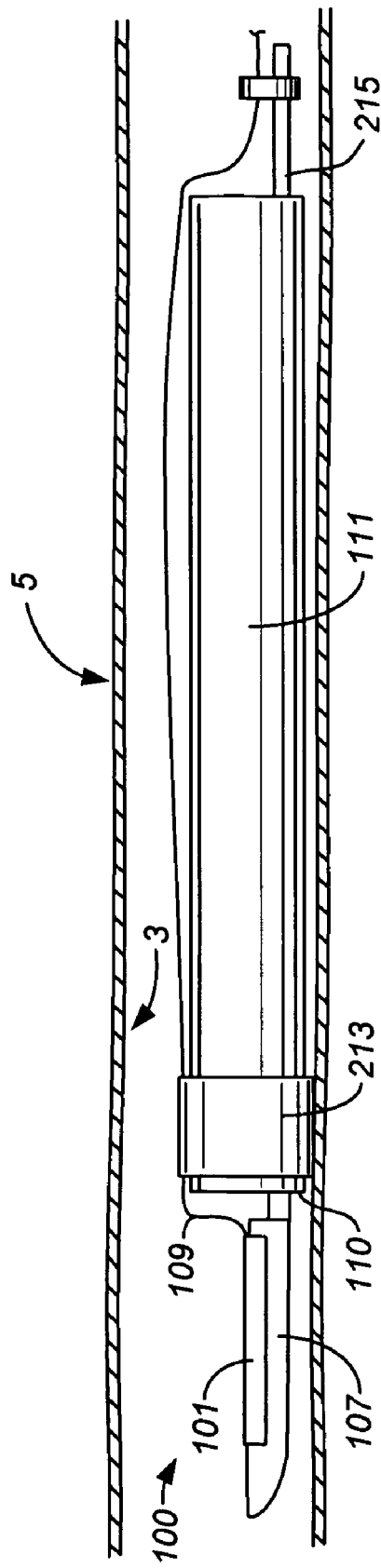
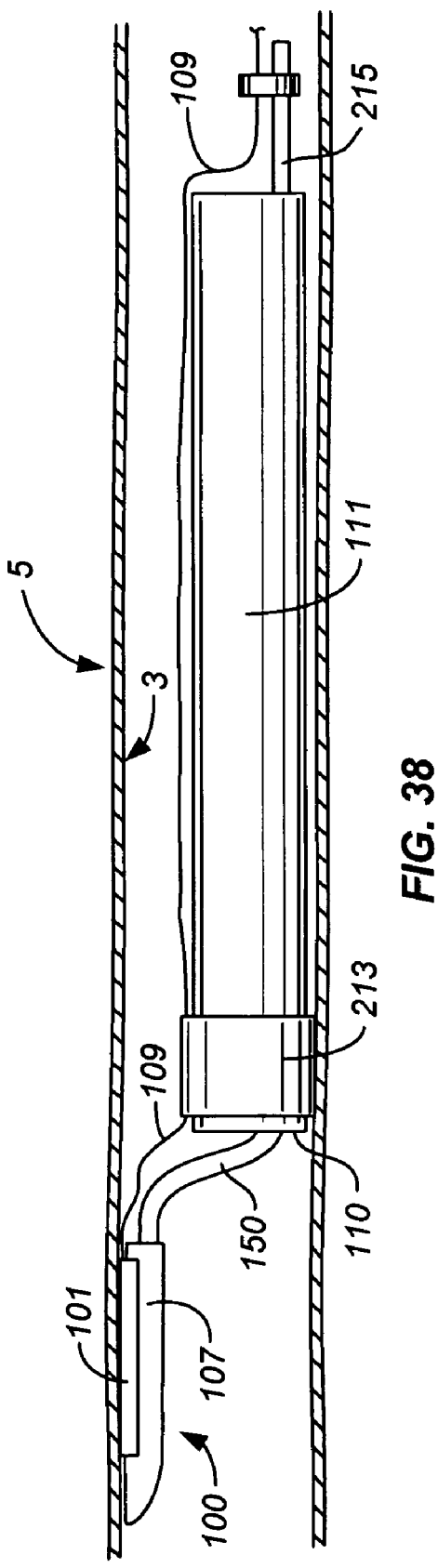
FIG. 37
FIG. 38

PRECISION ABLATING DEVICE

FIELD OF THE INVENTION

The invention relates to medical devices and methods of use thereof, for ablating tissue in an alimentary tract.

BACKGROUND OF THE INVENTION

Two of the major functions of the human esophagus are the transport of food from intake to the stomach and the prevention of retrograde flow of gastrointestinal contents. The retrograde flow is, in part, prevented by two esophageal sphincters which normally remain closed and which are functional rather than distinct entities. In particular, a lower esophageal sphincter normally remains closed until parasympathetic activation causes its relaxation, allowing food to pass into the stomach from the esophagus. Various types of food and other activity may cause relaxation of the sphincter, such as fatty meals, smoking and beverages having xanthene content. Certain drugs or pharmaceuticals also may cause relaxation of this lower esophageal sphincter, as well as localized trauma or other problems such as neuromuscular disorders.

Regardless, patients having such difficulties may present with clinical indications including dysphagia, or difficulty in swallowing, as well as more classic symptoms of heartburn and other similar complaints. Recurrent problems of this nature often lead to a disorder known as reflux esophagitis, consisting of esophageal mucosa damage due to the interaction of the gastric or intestinal contents with portions of the esophagus having tissue not designed to experience such interaction. As suggested above, the causative agent for such problems may vary. Esophagitis can lead to a pre-cancerous condition, known as Barrett's Esophagus, which occurs when cells of the mucosal lining become damaged and are at risk of neoplasia.

As described for example in copending, commonly owned U.S. application Ser. No. 10/754,445, filed Jan. 9, 2004, a treatment catheter having an expandable electrode support can be used for treating a circumferential region of the esophagus in order to ablate an abnormal mucosal layer of the esophagus using radiofrequency (RF) energy. When successful, the treatment results in regeneration of a normal mucosal layer substantially free from metaplastic and other damage epithelial cells characteristic of Barrett's Esophagus.

In some instances, however, such radiofrequency ablation treatment may not be entirely successful and one or more regions of abnormal mucosa may remain. Alternatively, some patients initially present to the physician with small discrete regions of abnormal mucosa that are better suited to for selective ablation rather than circumferential ablation.

SUMMARY OF THE INVENTION

In general, in one aspect, the invention features an ablation device including an ablation structure configured to be removably coupled to a distal end of an endoscope. The device includes a deflection mechanism adapted to move the ablation structure with respect to the endoscope and toward a tissue surface.

Implementations of the invention can include one or more of the following features. The ablation structure can include a plurality of electrodes. The device can also include a movement mechanism adapted to move the ablation structure with respect to the endoscope. The device can include a coupling mechanism adapted to fit over an outside surface of an endoscope to couple the ablation structure with the endoscope.

The device can also include a sheath adapted to be unrolled over the outside surface of the endoscope to couple the ablation structure to the endoscope. The sheath can alternatively be adapted to couple the ablation structure to the endoscope. In this embodiment the sheath includes a slit formed in a proximal portion of the sheath, the slit being adapted to be opened to admit a distal end of an endoscope into the sheath. In another embodiment, a sheath can include a distal portion with a smaller outer diameter than a proximal portion of the sheath, the distal portion of the sheath being adapted to be expanded when an endoscope is inserted into it.

The device can include a coupling mechanism adapted to permit the ablation structure to pivot with respect to the endoscope when coupled to the endoscope. The coupling mechanism can include a ring wherein the ablation structure is adapted to pivot about the ring. In another embodiment, the coupling mechanism can include an elastic band adapted to flex to permit the ablation structure to pivot. The coupling mechanism of the device can be adapted to fit within a channel of the endoscope to couple the ablation structure with the endoscope.

Where the device includes a coupling mechanism, the ablation structure of the device can be adapted to fit within the endoscope channel. Additionally, the deflection mechanism can be adapted to fit within the endoscope channel. In one embodiment, the ablation structure is mounted on the deflection mechanism. In one embodiment, the coupling mechanism comprises a shape memory member and the deflection mechanism comprises a bent portion of the shape memory member.

Implementations of the invention can include one or more of the following features. The ablation structure can be further adapted to move from a first configuration to a second radially expanded configuration. In one embodiment, the device further includes an ablation structure actuator adapted to move the ablation structure from the first configuration to the second configuration.

The deflection mechanism of the device can include an inflatable member and/or an expandable member.

Implementations of the invention can include one or more of the following features. The device can include a torque transmission member adapted to transmit torque from a proximal end of the endoscope to the ablation structure to rotate the ablation structure about a central axis of the endoscope. The torque transmission member can include first and second interlocking members adapted to resist relative rotational movement between the endoscope and the ablation structure about the central axis. The first interlocking member can be a key and the second interlocking member can be a keyway. In one embodiment, the first interlocking member is attached to a sheath surrounding the endoscope and the second interlocking member is attached to a catheter supporting the ablation structure. In a further embodiment, the catheter and sheath are adapted for relative movement along the central axis.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a view of the ablation device of the invention.

FIG. 2 is an end view of the ablation device of the invention.

FIG. 3 is an end view of the device in an expanded configuration.

FIG. 4 is a view of a coupling mechanism of the device.

FIG. 5 is a view of the ablation device of the invention showing an alternative coupling mechanism.

FIG. 9 is a view of the ablation device of the invention in an unexpanded configuration.

FIG. 10 is a view of the ablation device of the invention in an expanded configuration.

FIG. 37 is an illustration of the ablation device of the invention including an alternative deflection member positioned within an esophagus in a non-deflected position.

FIG. 38 is an illustration of the device shown in FIG. 37 wherein the deflection member is in a deflected position.

DETAILED DESCRIPTION OF THE INVENTION

Figure 19:
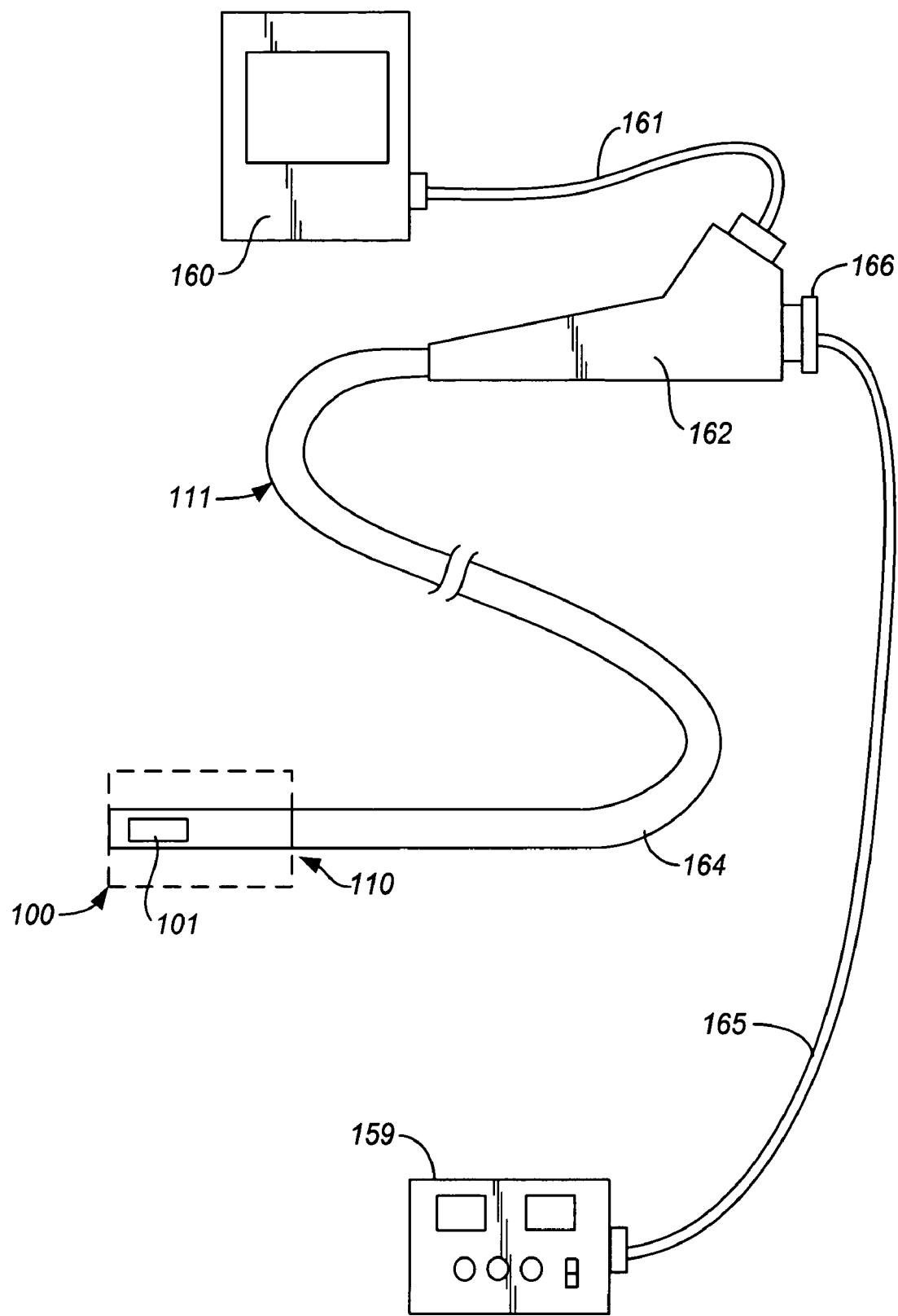
FIG. 19 is an illustration of the ablation device of the invention combined with an endoscope system.

A method of ablating tissue in an alimentary tract comprises the use of an ablation device including an ablation structure supported by conventional endoscopes 111, as illustrated in FIG. 19. An example of one commercially available conventional endoscope 111 is the Olympus "gastrovideoscope" model number GIF-Q160. While the specific construction of particular commercially available endoscopes may vary, as shown in FIG. 19, most endoscopes include a shaft 164 having a steerable distal end 110 and a hub or handle 162 which includes a visual channel 161 for connecting to a video screen 160 and a port 166 providing access to an inner working channel within the shaft 164. Dials, levers, or other mechanisms (not shown) will usually be provided on the handle 162 to allow an operator to selectively steer the distal end 110 of the endoscope 111 as is well known in the endoscopic arts. In accordance with the present invention, an ablation device, including an ablation structure is advanced into the alimentary tract while supported at the distal end of an endoscope. The ablation structure is deflectable toward a tissue surface and the ablation structure is activated to ablate the tissue surface. Within the alimentary tract, variously sized tissue surface sites, can selectively be ablated using the device.

Figure 20:
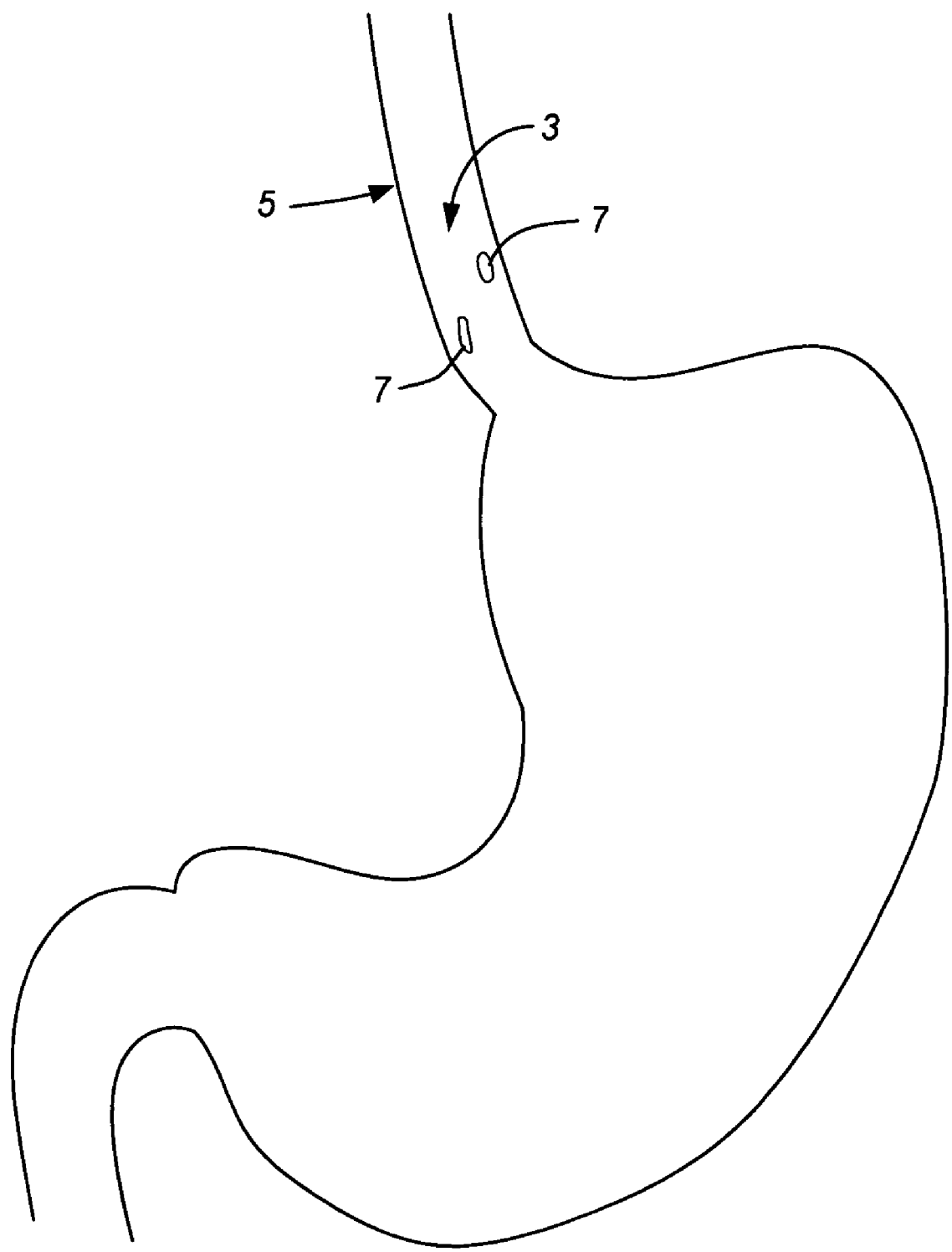
FIG. 20 is a schematic of view of portions of the upper digestive tract in a human, showing an esophagus including abnormal mucosa.
Figure 21:
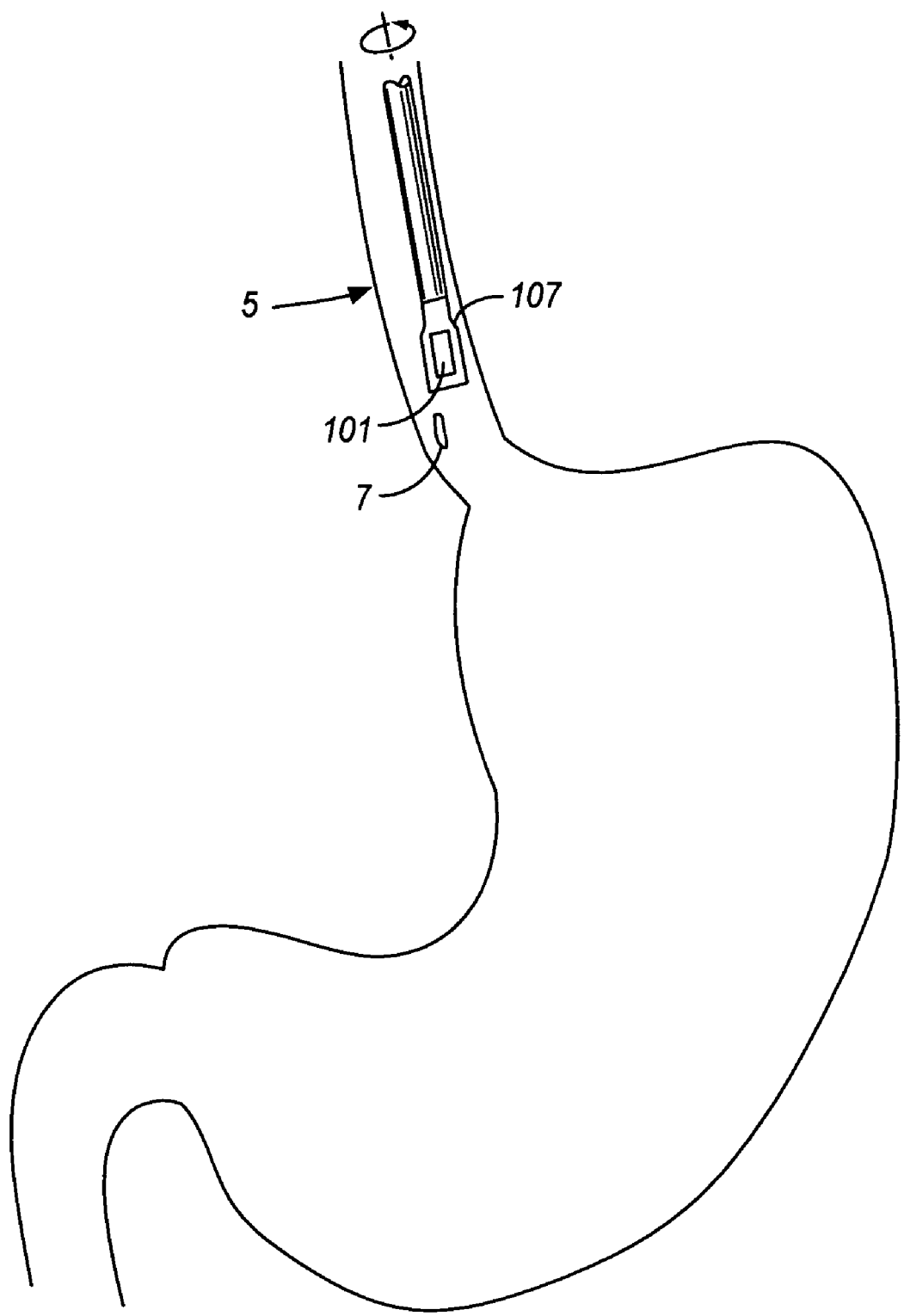
FIG. 21 is an illustration of the ablation device of the invention positioned within the esophagus.

In general, in one aspect a method of ablating tissue in an alimentary tract is provided. The method includes advancing an ablation structure into the alimentary tract while supporting the ablation structure with an endoscope. The method further includes moving at least part of the ablation structure with respect to the endoscope and toward a tissue surface; and activating the ablation structure to ablate the tissue surface. Moving at least a portion of the ablation structure with respect to the endoscope can include, but is not limited to movement toward, away from or along the endoscope. As shown in FIGS. 1, 2, 3 and 21, in one aspect a method of ablating tissue in an alimentary tract includes an ablation device 100 for ablating a tissue surface 3, wherein the device 100 includes an ablating structure, for example, an ablation structure 101 supported by an endoscope 111. The method includes ablating tissue in an alimentary tract by the steps of 1) advancing the ablation structure 101 into the alimentary tract; 2) deflecting the ablation structure 101 toward a tissue surface 3; and 3) activating the ablation structure to ablate the tissue surface 3. As shown in FIG. 1, the device 100 can additionally include a housing 107, electrical connections 109, an inflation line 113 and an inflation member 105. For the purposes of this disclosure, any components made up of mucous membrane and muscle extending between the mouth and the anus; functioning in digestion and elimination are contemplated as part of the alimentary tract. Such components include but are not limited to the esophagus, stomach, small intestine, appendix, large intestine, colon, and rectum. As shown in FIGS. 20 and 21 the alimentary tract can include the esophagus 5, wherein abnormal mucosa 7 can be treated using the ablation structure 101.

The ablation structure 101, in one embodiment is an electrode structure configured and arranged to deliver energy comprising radiofrequency energy to the esophageal mucosa. It is envisioned that such an ablation structure 101 can include a plurality of electrodes. For example, two or more electrodes could be part of an ablation structure. The energy may be delivered at appropriate levels to accomplish ablation of mucosal or submucosal level tissue, or alternatively to cause injury to these tissues, while substantially preserving muscularis tissue. The term "ablation" as used herein means thermal damage to the tissue causing tissue or cell necrosis. Thermal damage can be achieved through heating tissue or cooling tissue (i.e. freezing). Typically, ablation in the present embodiments is designed to remove the entire mucosal lining in the treatment region, including the abnormal mucosa 7, for example, abnormal columnar growths, from the portions of the esophagus 5 so affected, and allow re-growth of a normal mucosal lining (see FIG. 21). Advantageously, healing is more rapid and stricture formation in the tissues is minimized when such an approach is used.

Although radiofrequency energy is one advantageous form of energy for ablation, it is recognized that other advantageous energy forms including, for example, microwave energy, or photonic or radiant sources such as infrared or ultraviolet light, the latter possibly in combination with improved sensitizing agents. Photonic sources can include semiconductor emitters, lasers, and other such sources. It is also recognized that another embodiment of this invention may utilize heatable fluid or a cooling media such as liquid nitrogen, Freon®, non CFC refrigerants or $CO_2$ as an ablation energy medium. For ablations using hot or cold fluids or gases, it is envisioned that the ablation system may require a means to circulate the heating/cool media from outside the patient to the heating/cooling balloon or other element and then back outside the patient again. Means for circulating media in cryosurgical probes are well known in the ablation arts. For example, and incorporated by reference herein, suitable circulating means are disclosed in U.S. Pat. No. 6,182,666 to Dobak, III; U.S. Pat. No. 6,193,644 to Dobak, III et al.; U.S. Pat. No. 6,237,355 to Li; and U.S. Pat. No. 6,572,610 to Kovalcheck et al.

In a particular embodiment, the energy delivered to the esophageal mucosa comprises radiofrequency energy that can be delivered from the energy delivery device 100. Radio frequency energy can be delivered in a number of ways. Usually, the radiofrequency energy will be delivered in a bipolar fashion from a bipolar array of electrodes positioned on the ablation structure 101, in some cases on an expandable structure, such as a balloon, frame, cage, or the like, which can expand and deploy the electrodes directly against or immediately adjacent to the mucosal tissue (e.g., through direct contact or through a dielectric membrane or other layer). Alternatively, the electrode structure may include a monopolar electrode structure which is energized by a radiofrequency power supply in combination with a return electrode typically positioned on the patient's skin, e.g., on the small of the back. In either case, the radiofrequency energy will typically be delivered at a high energy flux over a very short period of time in order to injure or ablate only the mucosal or submucosal levels of tissue without substantially heating or otherwise damaging the muscularis tissue. Wherein the ablation structure includes a plurality of electrodes, one or more of the electrodes can be bipolar or monopolar. Combinations of bipolar and monopolar electrodes are envisioned. To achieve controlled ablation depths the spacing between the electrodes can modified. Electrode gaps can range from 0.1 mm to 20 mm.

The ablation structure 101 can be arranged and configured in any of a number ways with regard to shape and size. Typically, the array has an area in the range from substantially 0.5 $cm^2$ to 9.0 $cm^2$. Typical shapes would include rectangular, circular or oval. In one embodiment, the ablation structure 101 has an area of 2.5 $cm^2$. In another embodiment, the ablation structure 101 has an area of 4 $cm^2$ and dimensions of 2 cm×2 cm.

The housing 107 is arranged and configured to support the ablation structure 101. The housing 107 can be made of any suitable material for withstanding the high energy flux produced by the ablation structure 101. As shown in FIGS. 1, 2, 3, 6, 11, 12, 16 and 17, in one embodiment, the housing 107 is sandwiched between the ablation structure 101 and an endoscope 111 when the ablation device 100 is supported by an endoscope 111. One end of the ablation structure 101 can be further away from the endoscope than the other end to improve ease of contact with the targeted tissue (not shown). For example, to ensure the proximal end of the ablation structure 101 makes contact with the targeted tissue, the proximal end of the electrode could be supported by a tapered housing member 107 (not shown).

The electrical connections 109 of the ablation device connects the ablation structure 101 to a power source. The electrical connections 109 can include a single wire or plurality of wires as needed to provide controlled energy delivery through the ablation structure 101. In one embodiment, the electrical connections 109 include low electrical loss wires such as litz wire.

The inflation line 113 is arranged and configured to transport an expansion medium in the form of fluid or gas to and from the inflation member 105. In one embodiment, the inflation line is a flexible tube. The inflation line 113 can be made of polymer or co-polymers, for example polyimide, polyurethane, polyethylene terephthalate (PET), polyamides (nylon) or the like. Typically, the expansion medium is a suitable fluid or gas.

Figure 27:
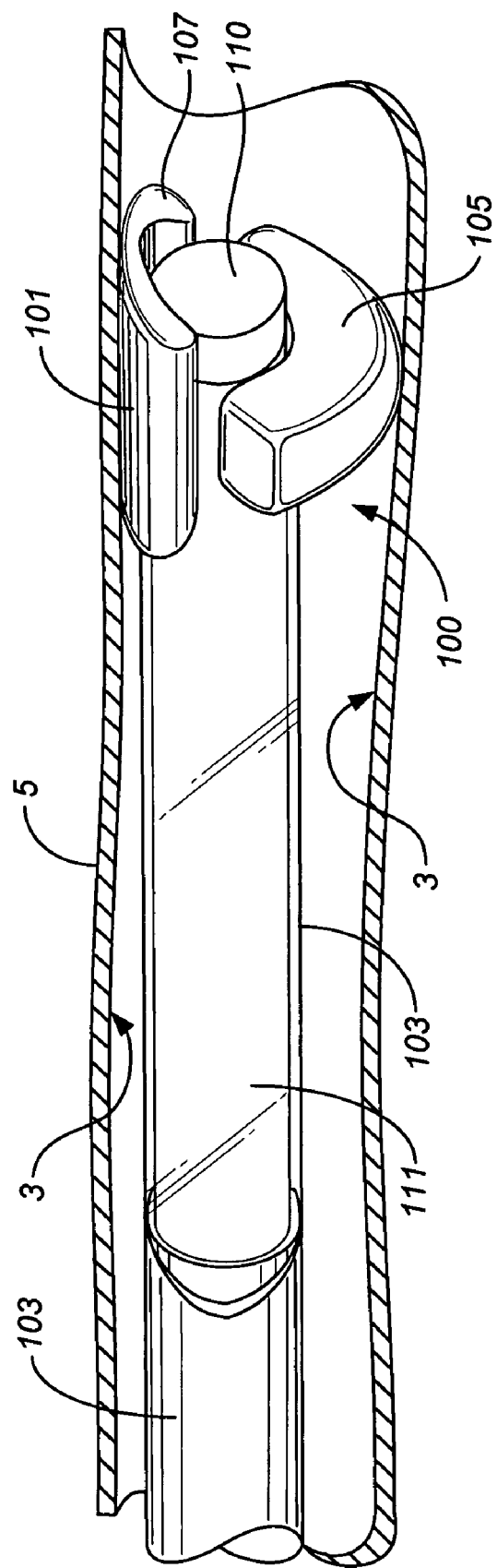
FIG. 27 is an illustration of the ablation device of FIG. 26 positioned within an esophagus.
Figure 41:
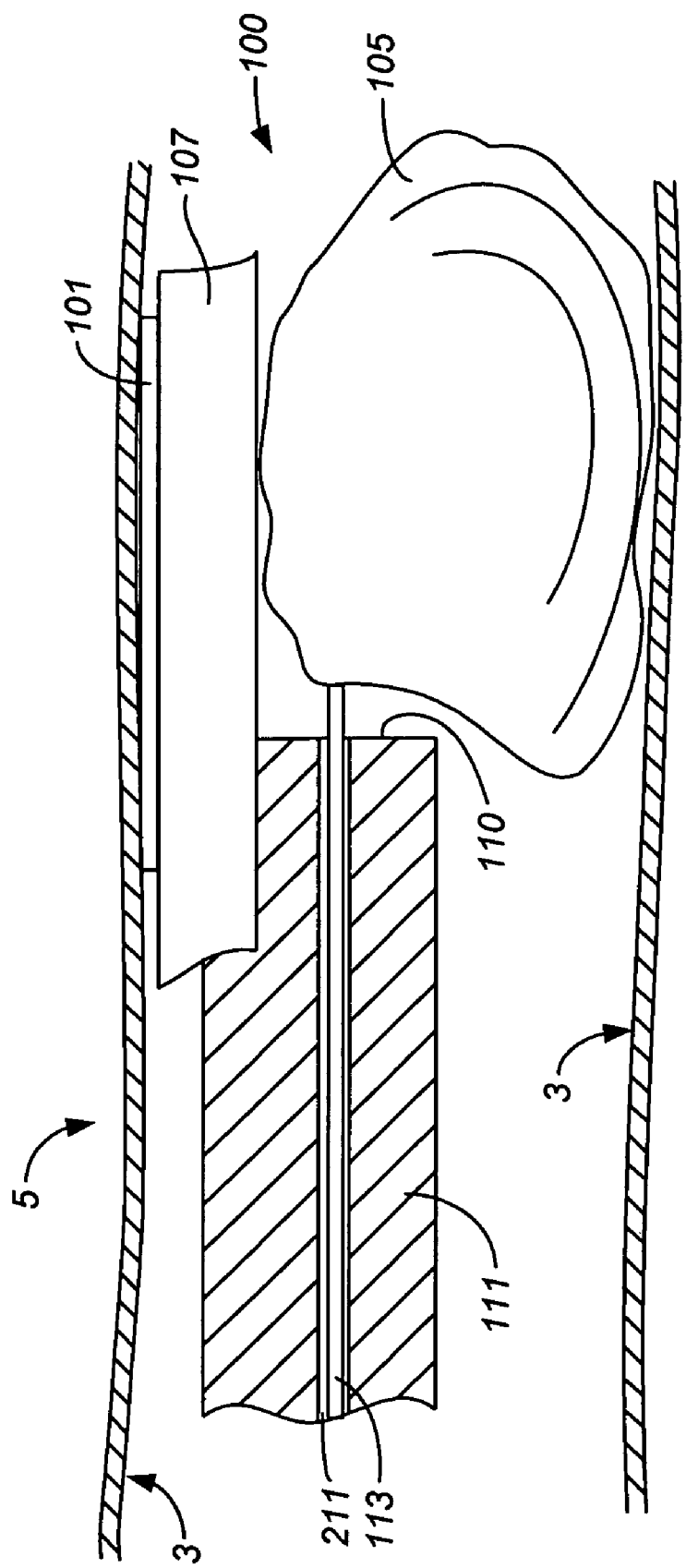
FIG. 41 is an illustration showing a cross sectional view of the ablation device of the invention positioned within an esophagus.
Figure 43:
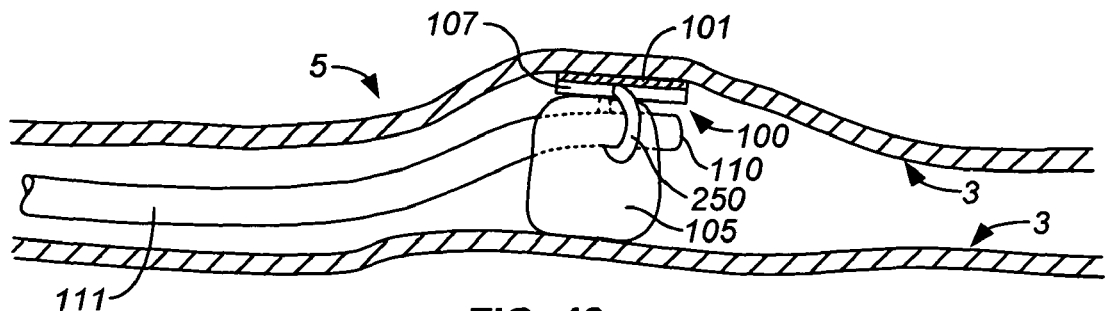
FIG. 43 is an illustration of the ablation device of the invention positioned within an esophagus showing a rotational feature combined with an inflation member in an expanded configuration.

The inflation member 105 is designed to deflect the ablation device 100 in relation to a tissue surface 3. The inflation member 105 can be reversibly expanded to an increased profile. In one embodiment, the inflation member 105 additionally serves as an attachment means for support of the ablation device 100 by an endoscope 111. As shown in FIGS. 2, 3, 9, 10, 11, 12, 16, 17 the inflation member 105 can be deployed from a low profile configuration or arrangement (see FIGS. 2, 9, 12, and 16) to an increased profile configuration or arrangement (see FIGS. 3, 10, 11, and 17) using the expansion medium. In preparation for ablation, when the inflation member 105 is sufficiently inflated, deflection of the ablation device 100 in relation to a tissue surface 3 can be achieved. As shown in FIGS. 3, 27, 41 and 43, in one embodiment, deflection of the ablation device 100 results in direct and sustainable contact between the ablation structure 101 of the device 100 and the tissue surface 3. For example, as shown in FIGS. 27, 41 and 43, when the inflation member 105 is sufficiently inflated, the resulting expanded profile of the inflation member 105, which contacts the tissue surface 3, results in contact by deflection between the tissue surface 3 of the inner wall of the esophagus 5 and the ablation structure 100. It is envisioned that suction can be applied in combination with the inflation member 105 to achieve contact between the ablation structure 101 and the tissue surface 3 (not shown). Suction could be achieved through the endoscope 111 or through the ablation device 100 to aid in collapsing the targeted tissue surface 3 around the ablation structure 101.

The inflation member 105 can be designed to be compliant, non-compliant or semi-compliant. The inflation member 105 can be made of a thin, flexible, bladder made of a material such as polymer, for example polyimide, polyurethane, polyethylene terephthalate (PET), or the like. In one embodiment, the inflation member is a balloon. Inflation of the inflation member 105 can be achieved through the inflation line 113 using, for example, controlled delivery of fluid or gas expansion medium. The expansion medium can include a compressible fluid such as air. The expansion medium may alternatively comprise an incompressible fluid, such as water, saline solution or the like.

Figure 6:
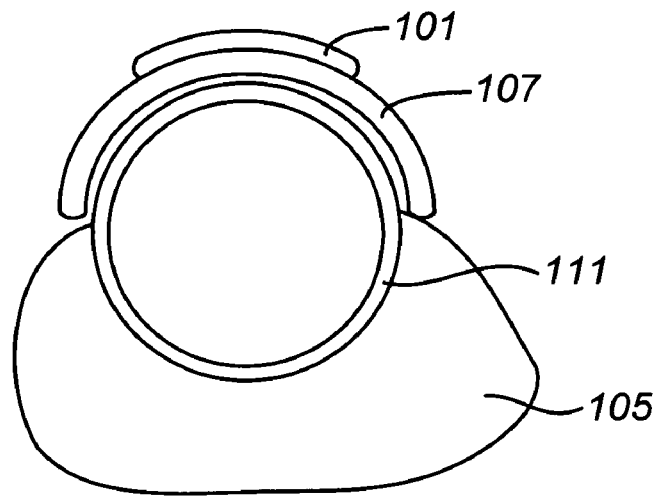
FIGS. 6, 7, and 8 are end views of the device in alternative expanded configurations.
Figure 7:
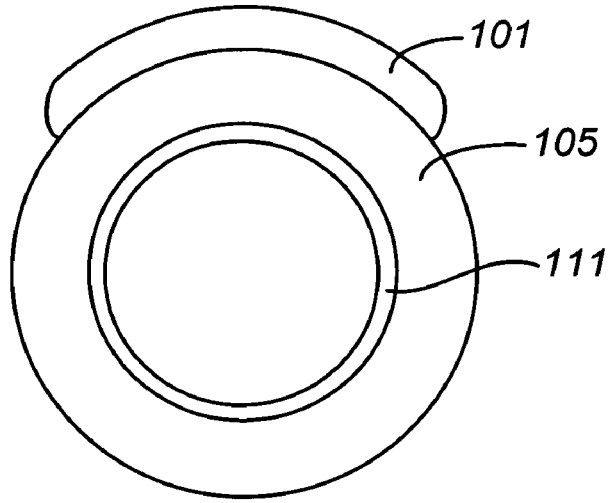
Figure 8:
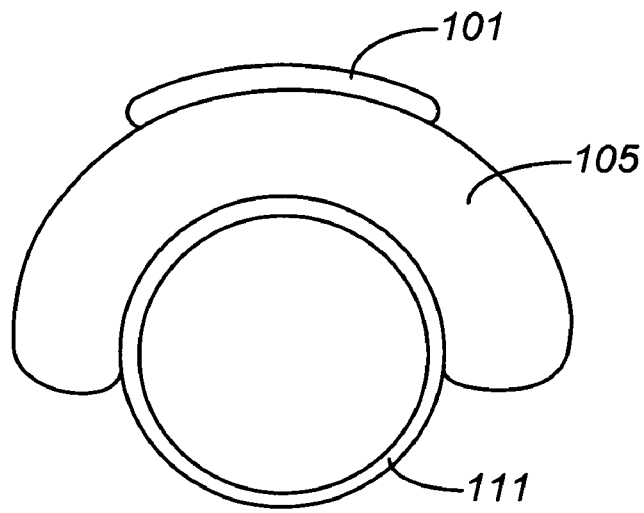
Figure 11:
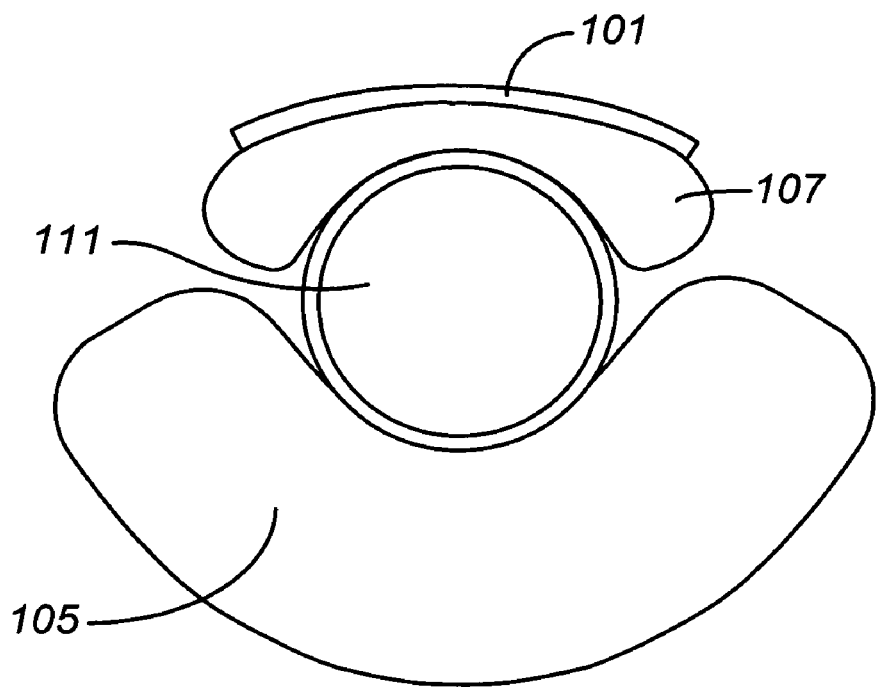
FIGS. 11 and 12 are end views of the device in an expanded configuration.
Figure 12:
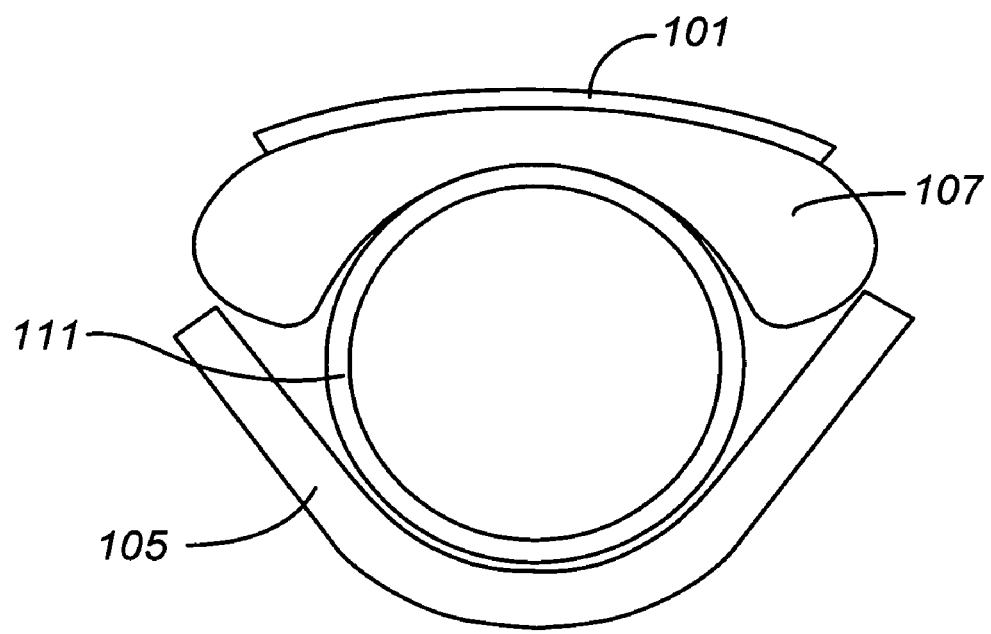

As shown in FIGS. 6, 7 and 8, the inflation member 105 can be configured and arranged in a variety of ways to facilitate deflection of the ablation device 100 in relation to a tissue surface 3. For example, as shown in FIG. 6, the inflation member 105 can be eccentrically positioned in relation to the supporting endoscope 111 as well as the housing 107 and the ablation structure 101. Alternatively, as shown in FIG. 7, the inflation member 105 can be positioned concentrically in relation to the supporting endoscope 111 and the ablation structure 101 can be attached to the inflation member 105 distally from the endoscope 111. In another embodiment, as shown in FIG. 8, the inflation member 105 can be positioned between the supporting endoscope 111 and the ablation structure 101. The ablation structure 101 shown in FIGS. 7-8 can cover a range of circumferences of the endoscope 111 spanning from 5 to 360 degrees when inflation member 105 is deployed.

One method of ablating tissue in an alimentary tract can include a first step of advancing an ablation structure 101, into the alimentary tract. In a second step, the ablation structure 101 is supported with an endoscope 111 within the alimentary tract. In a third step, the ablation structure 101 is deflected toward a tissue surface 3. In a forth step, energy can be applied to the ablation structure 101 to ablate the tissue surface 3.

In another method, the step of advancing an endoscope-supported ablation structure 101 can include advancing the endoscope 111 into the alimentary tract and advancing the ablation structure 101 over the endoscope 111. For example, the endoscope 111 can be positioned relative to an ablation target tissue surface 3 after which the ablation structure 101 can be advanced over the outside of the endoscope 111 for ablating the target tissue surface 3.

In a further method, the step of supporting the ablation structure 101 with an endoscope 111 includes inserting the endoscope 111 into the ablation structure 101 (see for example, FIG. 1). In one related method, the ablation structure 101 is supported by a sheath 103 (see FIGS. 13 and 22-24, 26-29, 30B, 31, 32 and 46) and the step of inserting the endoscope 111 into the ablation structure 101 includes inserting the endoscope 111 into the sheath 103. In a further related method, the step of inserting the endoscope 111 into the sheath 103 includes creating an opening in the sheath 103 (not shown).

In a particular method, a distal portion of a sheath 103 having a smaller outer diameter than a proximal portion of the sheath 103, is adapted to be expanded when an endoscope 111 is inserted into it.

In another method, the step of advancing the ablation structure 101 into the alimentary tract includes advancing the ablation structure 101 through a channel of the endoscope 111 from either the endoscopes proximal or distal end (see as discussed below for FIGS. 33A, 34A and 35A). In yet another method, the step of supporting the ablation structure 101 comprises supporting the ablation structure 101 with a channel of the endoscope (see as discussed below for FIGS. 33A, 34A, 35A, 36-39 and 40). In a further method, a deflection structure or deflection member 150 is advanced through a channel of the endoscope 111 and the step of deflecting the ablation structure 101 toward a tissue surface 3 includes deflecting the ablation structure 101 with the deflection structure or deflection member 150 (see as discussed below for FIGS. 33A, 33B, 34A, 34B, 35A, 35B, 36-38 and 41).

Figure 33A:
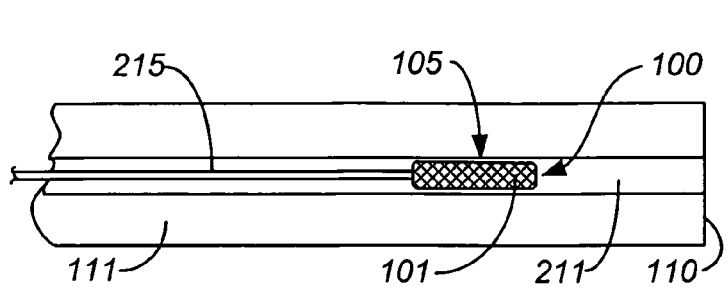
FIG. 33A is a cross sectional view of the device positioned within an endoscope internal working channel wherein an inflatable member feature is in an unexpanded position.
Figure 33B:
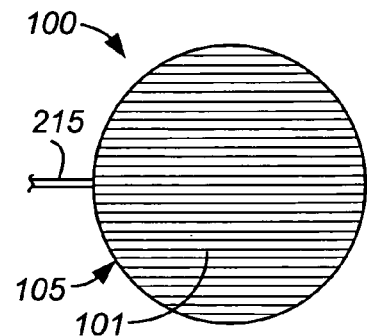
FIG. 33B is a view of the device shown in FIG. 33A wherein the inflatable member feature is in an expanded position.
Figure 34A:
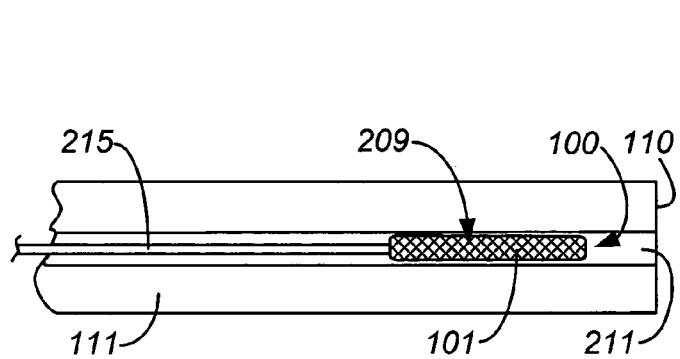
FIG. 34A is a cross sectional view of the device positioned within an endoscope internal working channel wherein an expandable member feature is in an unexpanded position.
Figure 34B:
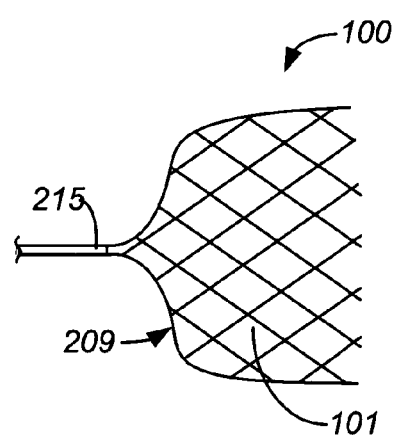
FIG. 34B is a view of the device shown in FIG. 34A wherein the expandable member feature is in an expanded position.
Figure 35A:
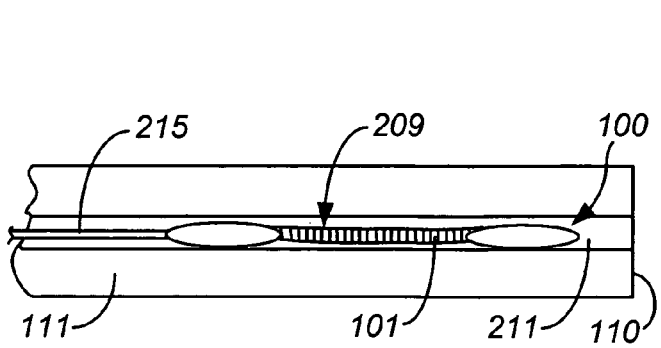
FIG. 35A is a cross sectional view of the device positioned within an endoscope internal working channel wherein an alternative expandable member feature is in an unexpanded position.

As illustrated in FIGS. 33A, 34A, and 35A, variously adapted and configured ablation structures 101 can fit within and be conveyed through an endoscope internal working channel 211. In each case, the ablation structure 101 and accompanying deflection mechanism can be conveyed through the internal working channel 211 in a dimensionally compacted first configuration that is capable of expansion to a second radially expanded configuration upon exiting the distal end 110 of the endoscope 111 (See for example, FIGS. 33A, 33B, 34A, 34B, 35A and 35B).

As shown in FIG. 33B, in one embodiment, the deflection mechanism is an inflation member 105, to which the ablation structure 101 can be integrated within or mounted/attached to, for example by etching, mounting or bonding. The inflation member 105 can be, for example, a compliant, non-compliant or semi-compliant balloon.

Figure 35B:
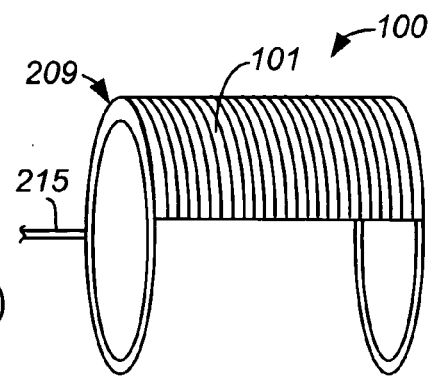
FIG. 35B is a view of the device shown in FIG. 35A wherein the expandable member feature is in an expanded position.

As shown in FIGS. 34B and 35B, in another embodiment, the deflection mechanism is an expandable member 209 that can expand to a second desired arrangement and configuration. As shown in FIG. 34B, the expandable member 209, can be an expandable stent, frame or cage device, to which an ablation structure 101 is mounted or integrated. For example, where the expandable member 209 is a wire cage, the wires can be a component of a bipolar circuit to provide the ablation structure 101 feature. Alternatively, the cage can have a flexible electrode circuit bonded or can be attached to an outer or inner surface of the cage to provide an ablation structure 101 that is an electrode. As shown in FIG. 35B, the expandable member 209, can be a folded or rolled series of hoops including or having an attached ablation structure 101 that expands upon exiting the endoscope distal end 110.

Figure 36:
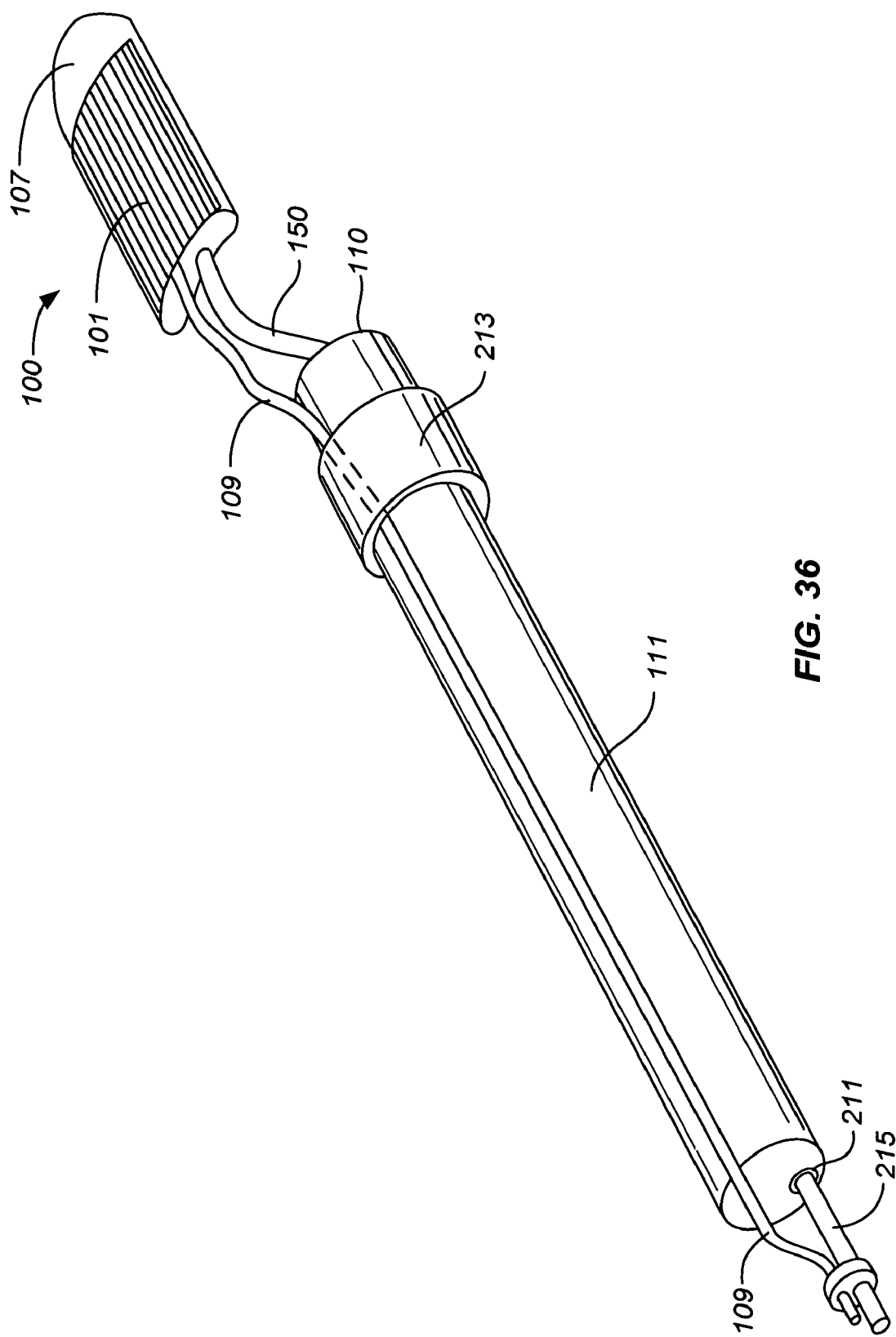
FIG. 36 is a view of the ablation device of the invention including an alternative deflection member.

As further illustrated in FIGS. 36-40, the ablation structure 101 can be supported with a channel of the endoscope 111. In one embodiment as shown in FIGS. 36-38, an ablation device 100 includes a deflection member 150 that supports an attached housing 107 and ablation structure 101. As shown in FIG. 36, the endoscope 111 includes an internal working channel 211 suitable for advancing or retreating the deflection member 150 which is connected to an internal coupling mechanism 215 of the ablation device 100. Both FIG. 36 and FIG. 38 show the deflection member 150 including a bent region of the deflection member 150 in a deployed position, wherein the deflection member 150 bent region is positioned external to the endoscope distal end 110. FIG. 37 shows the deflection member 150 in an undeployed position, wherein the deflection member 150 bent region is positioned internal to the endoscope 111. The ablation structure 101 is thus supported with a channel of the endoscope 111 (the internal working channel 211 of the endoscope 111) by way of the deflection member 150 and the connected internal coupling mechanism 215 of the ablation device 100.

In addition, when the deflection member 150 is advanced or moved proximally or distally within the endoscope internal working channel 211, the deflection member 150 is accordingly advanced through a channel of the endoscope 111. In another implementation, as shown in FIG. 41, wherein the deflection mechanism is an inflatable member 105 (shown in a deployed configuration) coupled to an inflation line 113, the inflation line 113 can be disposed within the endoscope internal working channel 211. In yet another implementation, both the inflatable member 105 (in an undeployed configuration) and inflation line 113 can be advanced within the internal working channel 211 either proximally or distally in relation to the endoscope 111 (not shown). Conductive wires 109 can pass through the working channel (not shown) or outside as shown in FIG. 36.

Figure 40:
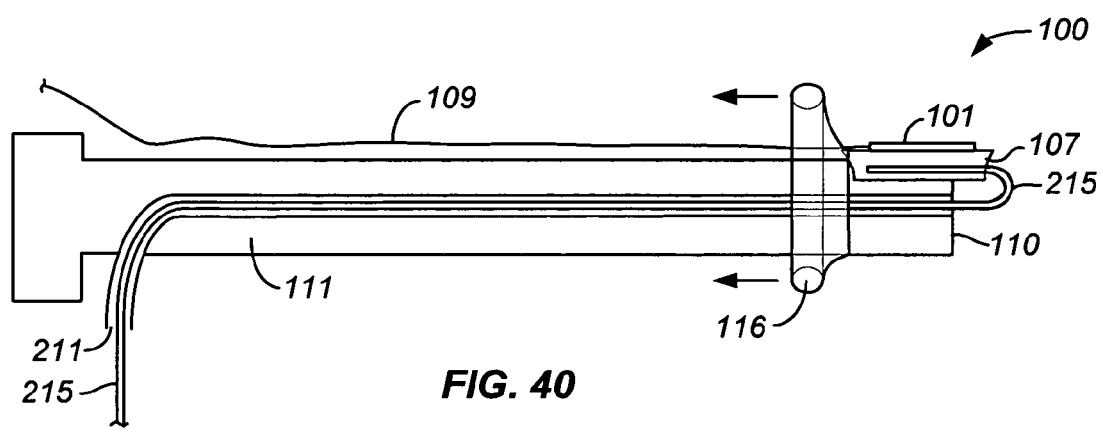
FIG. 40 is a cross sectional view of the ablation device of the invention showing an alternative internal coupling mechanism and a rolled sheath feature.

As shown in FIG. 40, in another implementation the endoscope 111 includes an internal working channel 211 suitable for supporting the ablation housing 107 and ablation structure 101 which are connected to an internal coupling mechanism 215 of the ablation device 100. As such, the connected ablation structure 101 is supported within a channel of the endoscope 111. Additionally as shown in FIG. 40, the housing 107 and ablation structure 101 can further be supported by an external region of the endoscope 111, wherein the internal coupling mechanism 215 is adapted and configured to position the housing 107 in contact with the external region of the endoscope 111. The internal coupling mechanism 215 can be cannulated (not shown) to facilitate use of the working channel to aspirate and inflate fluids or air.

In another ablation method, an additional step includes moving the ablation structure 101 with respect to the endoscope 111 within the alimentary tract. As illustrated in FIGS. 23, 24, 27, 28, 29, 31 and 46, and discussed below, a sheath 103 of the ablation device 100 to which the ablation structure 101 is attached can enable moving the ablation structure 101 with respect to the endoscope 111. Further, as illustrated in FIGS. 33A, 34A, 35A, 36, 37, 38 and 40, and discussed above, an internal working channel 211 of the endoscope 111 through which at least a part of the ablation device 100 is disposed can enable moving the ablations structure 101 with respect to the endoscope 111.

Referring to FIGS. 3, 27, 41 and 43, in yet another method, the step of deflecting the ablation structure 101 toward a tissue surface 3 includes inflating an inflation member 105 of the ablation device 100 within the alimentary tract. The inflation member 105 can be arranged and configured to be reversibly inflatable. The inflation member 105 can be inserted along with the ablation structure 101 into an alimentary tract 1 in a collapsed configuration and expanded upon localization at a pre-selected treatment area. In one implementation, the inflation member 105 is a balloon. For example, in FIGS. 3, 27, 41 and 43 it is shown how deflecting the ablation structure 101 toward a tissue surface 3 is achieved when the inflation member 105 is inflated or deployed. As illustrated in FIGS. 3, 27, 41 and 43, upon sufficient inflation, the inflation member 105 contacts a tissue surface 3 consequently deflecting the ablation structure 101 which contacts an opposing tissue surface 3.

Figure 13:
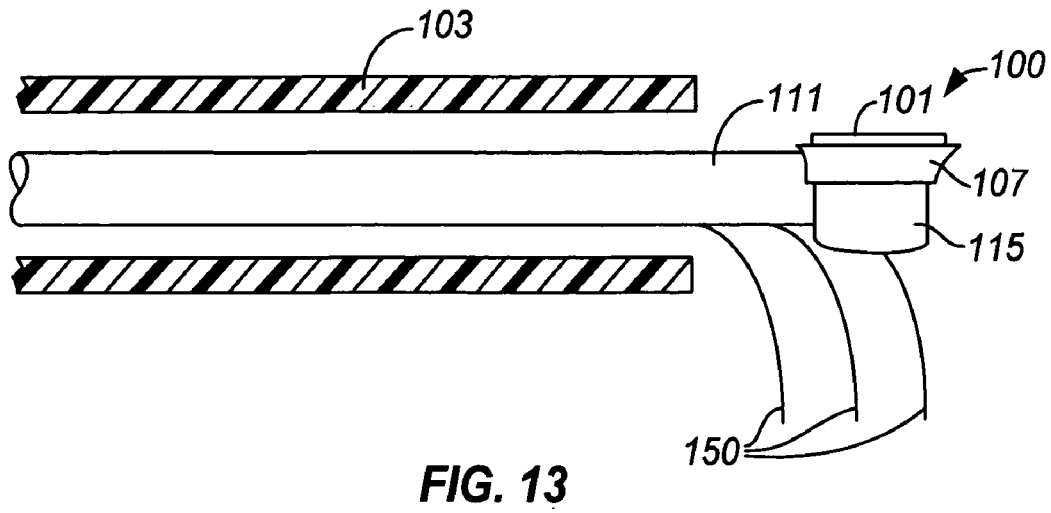
FIG. 13 is a view of the ablation device of the invention showing a deflection member feature.

As shown in FIGS. 13, 14, 15, 34, 35 and discussed above, in a further method, the step of deflecting the ablation structure 101 includes expanding a deflection structure or deflection member 150. In one implementation, as shown in FIG. 13, the ablation device 100 includes a sheath 103, wherein the sheath 103 is arranged and configured to receive the deflection member 150, the endoscope 111 and ablation structure 101 internally to the sheath 103. As shown in FIG. 13, the deflection member 150 can be a series of flexible extensions that deploy outwardly for deflecting the ablation device 100 when the deflection member 150 is extended beyond the end of the sheath 103. Conversely, the deflection member 150 can bend or fold when positioned within and moved internally to the sheath 103 (not shown). In one implementation, the deflection member 150 is a shape memory alloy, for example, Nitinol. The flexible extensions of the deflection member 150 in this embodiment can be coupled to the endoscope (as shown in FIG. 13), an elastomeric sheath 115 of the ablation device 100 (also shown in FIG. 13) or any part of the device 100, including the ablation housing 107.

As shown in FIGS. 33, 34, 35, 36, 37 and 38, and discussed above, in a further method, the step of deflecting the ablation structure 101 includes moving a deflection structure or deflection member 150.

Figure 18:
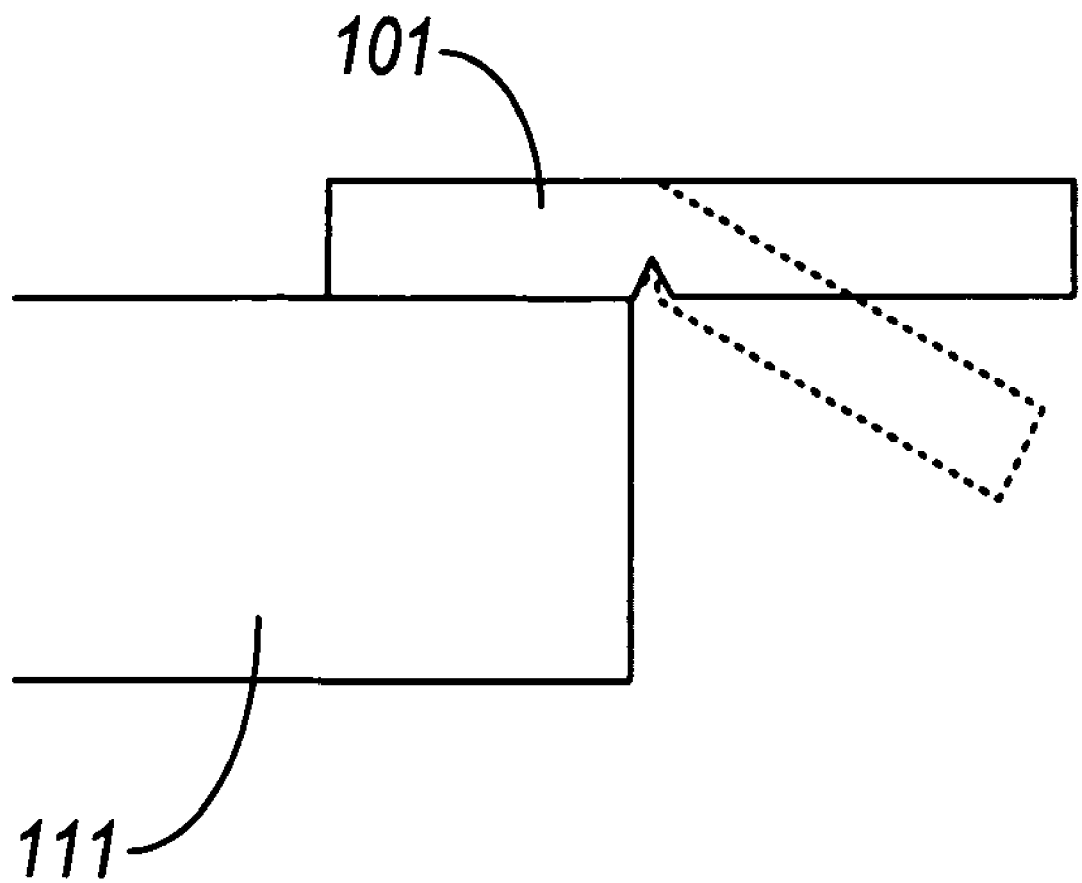
FIG. 18 is a view of the ablation device of the invention showing an ablation structure feature.

Briefly, in each case moving the deflection 150 is used to change the deflection member 150 from a non-deployed to a deployed configuration. As shown in FIG. 18, in one embodiment, deflecting the ablation structure 101 includes a flexing point in the ablation structure 101, wherein the ablation structure 101 can deflect in response to, for example, resistance met in contacting a tissue surface 3.

As shown in FIGS. 42, 43, 44A-C and discussed in detail below, in another method, the step of deflecting the ablation structure 101 includes but it not limited to rotating, pivoting, turning or spinning the ablation structure 101 with respect to the endoscope 111. Deflection of the ablation structure 101 with respect to the endoscope 111 can occur in combination with the endoscope 111 distal end 110 deflecting with respect to the alimentary tract or without. Also, the ablation structure 101 can deflect in combination with an inflation member 105used to achieve apposition of the ablation device 100 to the tissue. It is contemplated that the step of deflecting the ablation structure 101 may additionally include any combination of the above disclosed deflecting steps.

Figure 45A:
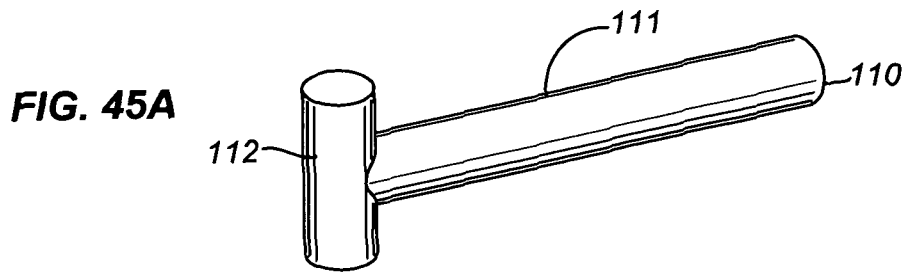
FIG. 45A is a view of an endoscope.
Figure 45B:
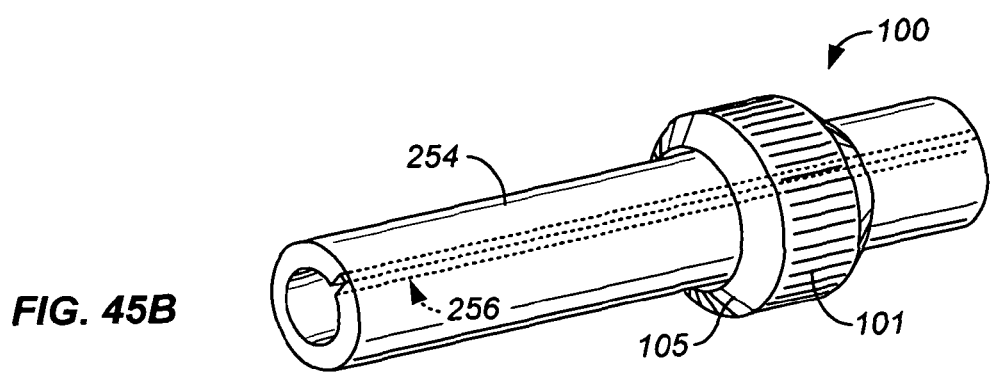
FIG. 45B is a view of the ablation device of the invention including a catheter feature.
Figure 46:
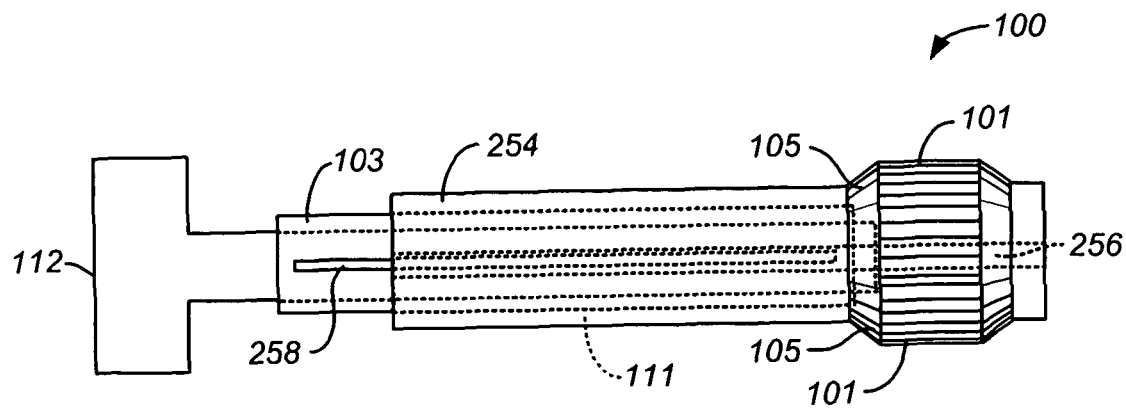
FIG. 46 is a view of the ablation device of the invention including the features shown in FIGS. 45A, 45B and 45C in an assembly.

As shown in FIGS. 14, 15, 16, 17, 33A, 33B, 34A, 34B, 35A, 35B, 45B and 46, in another ablation method, an additional step includes moving the ablation structure 10 1 from a first configuration to a second radially expanded configuration. The details regarding radial expansion of the ablation structure 101 shown in FIGS. 14, 15, 16 and 17 are described below, while the details for FIGS. 33A, 33B, 34A, 34B, 35A and 35B are described above. Additionally, as shown in FIGS. 45B and 46, the ablation structure 101 can be arranged in a first configuration wherein the ablation structure 101 is coupled directly or alternatively through an housing 107 (not shown) to an inflation member 105 attached to a catheter 254. In an undeployed configuration as shown in FIGS. 45B and 46, the non-inflated inflation member 105 and ablation structure 101 have a relatively low profile in relation to the endoscope 111. When deployed, the inflation member 105 moves the ablation structure 101 to a second radially expanded configuration (not shown).

As shown in FIGS. 4, 5, 9, 10, 39, 42, 43, 44A-C, 45B and 46, in a further method, an additional step includes attaching the ablation structure 101 to the endoscope 111. As shown in FIG. 4, attachment of the ablation structure 101 can be by way of a split sheath 106. In one implementation, the split sheath 106 is coupled to the housing 107 and fits over the outside of an endoscope 111 where it can be fastened to attach the ablation structure 101 to the endoscope 111 (not shown). As shown in FIG. 5, another feature for removably attaching the ablation structure 101 to the endoscope 111 is a spiral sheath 104. As illustrated in FIG. 5, an end of the spiral sheath 104 can be connected to the housing 107, while the body of the spiral sheath 104 coils around the outside of the endoscope 111. The spiral sheath 104 can additionally coil around both the electrical connections 109 and the inflation line 113 along a length of the endoscope 111. As shown in FIGS. 9 and 10, attachment of the ablation structure 101 to the endoscope 111 can also be by way of an elastomeric sheath 115 The elastomeric sheath 115 can removably hold the ablation structure 101 in a desired position on the endoscope 111. The elastomeric sheath 115 can be arranged and configured to fit over the endoscope distal end 110. As shown in FIGS. 9 and 10, the inflation member 105 can be attached to the elastomeric sheath 115 or alternatively the inflation member 105 can also act as the "elastomeric sheath" (not shown).

In another method, the step of attaching the ablation structure 101 to the endoscope 111 includes attaching the ablation structure 101 to an outside surface of the endoscope. Alternatively, the attaching step can include, for example, attaching to an inside surface, an outside or inside feature of the endoscope, or any combinations of the above. Lubricants such as water, IPA, jelly or oil could be use to aid attachment & removal of the ablation device from the endoscope.

As shown in FIG. 40, in a further method, the step of attaching the ablation structure 101 to the endoscope 111, includes an ablation structure 101 having an attached rolled sheath 116, wherein attaching the ablation structure 101 to the endoscope 111 includes unrolling the sheath 116 over an outside surface of the endoscope 111. The rolled sheath 116 can additionally cover the electrical connections 109 of the ablation device 100 along a length of the endoscope 111 (see FIG. 40). In a related method, the ablation structure 101 is attached to the endoscope 111 by an attaching step including unrolling the rolled sheath 116 over an outside surface of the endoscope 111 and part of the ablation structure 101 (not shown).

Figure 39:
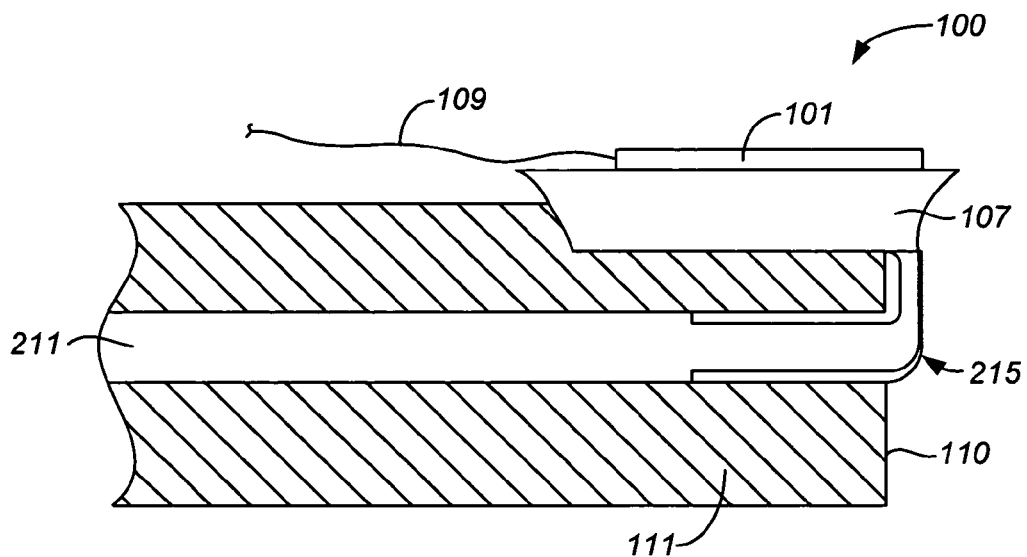
FIG. 39 is a cross sectional view of the ablation device of the invention showing an internal coupling mechanism feature.

In another method, as shown in FIG. 39, the step of attaching the ablation structure 101 to the endoscope 111 includes attaching the ablation structure 101 to a channel of the endoscope. As shown in FIG. 39, in one implementation, the housing 107 and ablation structure 101 are coupled to an internal coupling mechanism 215 that is positionable within an internal working channel 211 of the endoscope 111. The internal coupling mechanism 215 in FIG. 39 is shown as attached to the internal working channel 211 at the endoscope distal end 110. In this embodiment, the housing 107 and ablation structure 101 are shown in alignment with and coupled to an outside surface of the endoscope 111 near the distal end 110.

In one method of ablating tissue in an alimentary tract, the tissue surface 3 can include a first treatment area and activation of the ablation structure 101 step can include activation of the ablation structure 101 to ablate the first treatment area, and further include moving the ablation structure 101 to a second area without removing the ablation structure 101 from the patient and activating the ablation structure 101 to ablate the second tissue area 3 (see FIGS. 20 and 21). For example, as shown in FIG. 20, where two or more areas of the tissue surface 3 of an esophagus 5 include abnormal mucosa 7 spots, the first abnormal mucosa 20 can be ablated by directing the ablation structure 101 to the first spot and then activating the ablation structure 101 to ablate the tissue surface 3. Then, without removing the ablation structure 101 from the patient, the ablation structure 101 can be directed to the second abnormal mucosa 7 spot for ablation of the appropriate region of the tissue surface 3.

In general, in another aspect, an ablation device 100 is provided that includes an ablation structure 101 removably coupled to an endoscope distal end 110, and a deflection mechanism adapted and configured to move the ablation structure 101 toward a tissue surface 3 (see for example, FIGS. 1-3, 5-14, 16, 17, 22-24, 26-29, 32, 33A, 34A, 35A, 36, 37, 38, 41, 43 and 46).

In a related embodiment, the ablation device 100 additionally includes an ablation structure movement mechanism adapted to move the ablation structure 101 with respect to the endoscope 111. As discussed below and shown in FIGS. 22-24, 26-29, 31 and 32, the ablation structure movement mechanism can be a sheath 103 to which the ablation structure 101 is attached, wherein the sheath 103 is arranged and configured to move the ablation structure 101 with respect to an endoscope 111 received within the sheath 103. Alternatively, as discussed above and shown in FIGS. 33A, 34A, 35A, 36, 37 and 38, the ablation structure movement mechanism can be in the form of an internal coupling mechanism 215 of the ablation structure 100, wherein the ablation structure is connected to the internal coupling mechanism 215 and at least a portion of the internal coupling mechanism 215 is disposed internally to the endoscope.

In another embodiment, the ablation device 100 additionally includes a coupling mechanism designed to fit over an outside surface of an endoscope 111, to couple the ablation structure 101 with the endoscope 111. For example, as discussed above and shown in FIG. 4, a split sheath 106 coupling mechanism is provided. Additionally, as discussed above, a spiral sheath 104, an elastomeric sheath 115, a rolled sheath 116 and an internal coupling mechanism as shown in FIGS. 4, 5, (9 and 10), 40 and 39 respectively, are examples of such coupling mechanisms. In a particular embodiment, the coupling mechanism includes a sheath 103 capable of supporting the ablation structure 101. It is contemplated that the sheath 103 can be tubing, a catheter or other suitable elongate members. The sheath 103 can be arranged and configured so that it can be moved independently of an associated endoscope.

As shown in FIG. 40, in another embodiment, the sheath 103 can be arranged and configured as a rolled sheath 116 that can be unrolled over the outside surface of the endoscope. In use, a rolled sheath 116 connected to the ablation device 100, for example at substantially near the proximal end of the housing 107 (from the perspective of an operator of the device), can be unrolled from such a position and continue to be unrolled toward the proximal end 112 of the endoscope 111 (see. FIG. 40). In this way, the rolled sheath 116 can be caused to contact and cover all or a portion of the length of the endoscope 111 (not shown). Additionally, as the rolled sheath 116 is unrolled along the endoscope 111, it can sandwich the electrical connections 109 between the rolled sheath 116 and the endoscope 111 (see generally FIG. 40).

Figure 26:
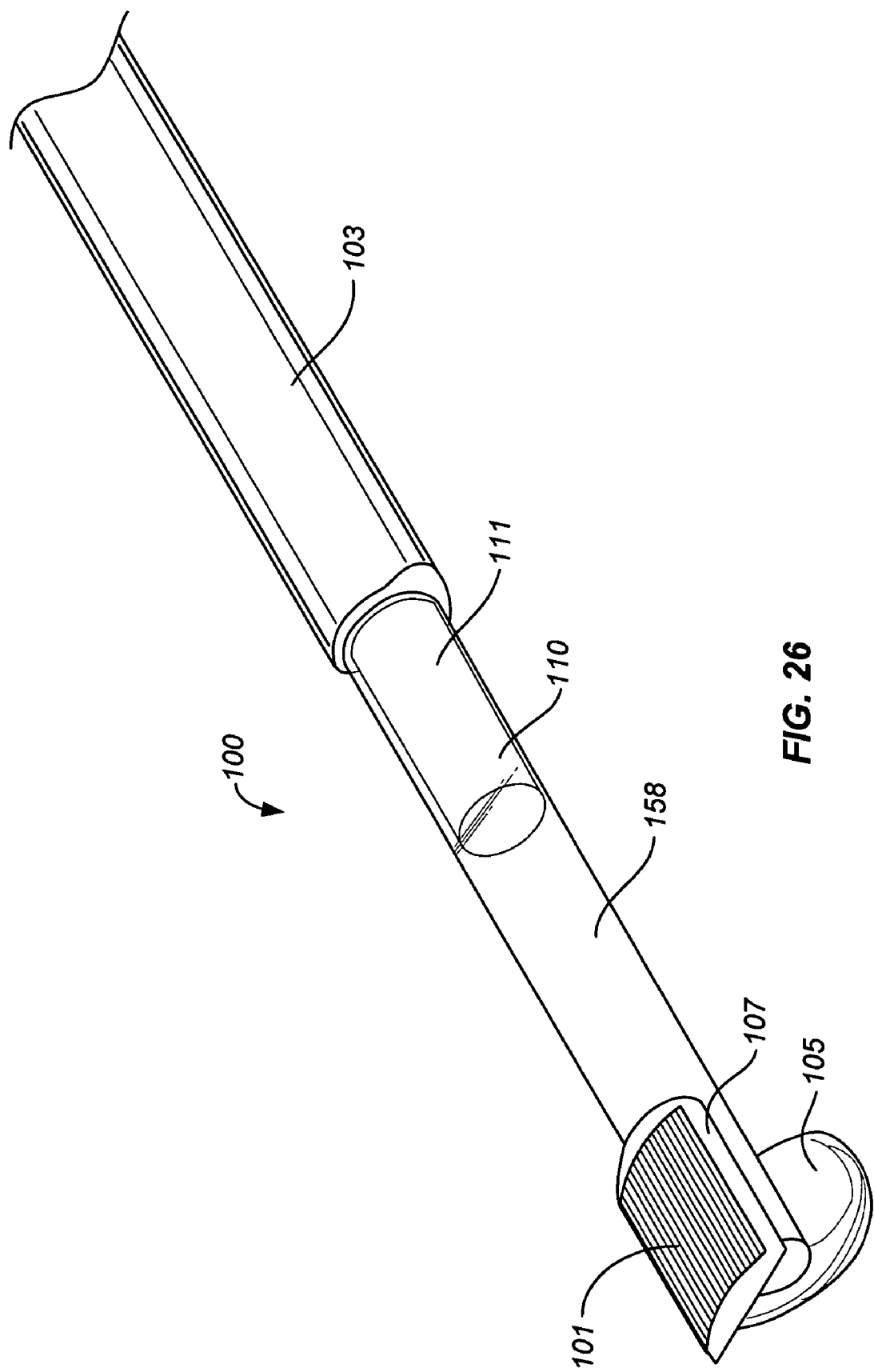
FIG. 26 is a view of the device including an alternative optically transmissive sheath feature and an inflation member feature in an expanded configuration.
Figure 31:
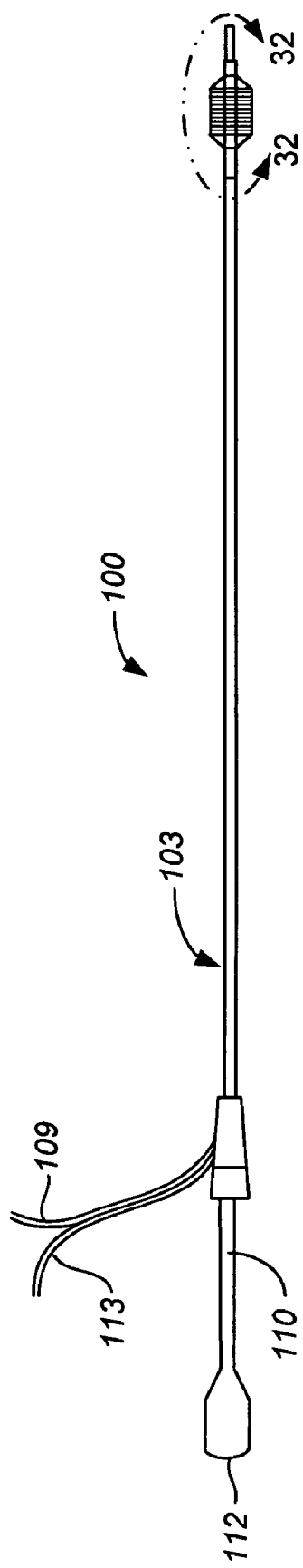
FIG. 31 is a view of the ablation device of the invention including an elongated sheath feature and an endoscope.
Figure 32:
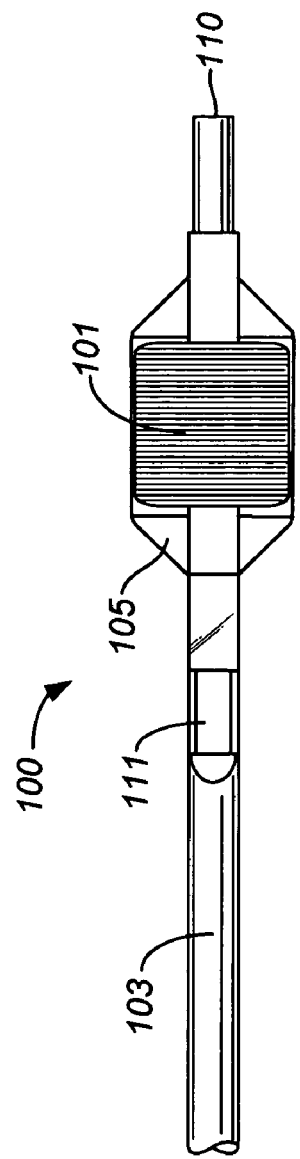
FIG. 32 is an enlarged view of the distal portion device of FIG. 31.

In another embodiment, as shown in FIGS. 26, 27, 31 and 32, the sheath 103 can be arranged and configured to support a deflection mechanism wherein the deflection mechanism includes a deflection structure or deflection member 150. As illustrated in FIGS. 26, 27, 31 and 32, where the deflection member 150 is an inflation member 105, the inflation member 105 can be directly attached to the sheath 103. As shown in each case, the inflation member 105 is positioned opposite the placement of the ablation structure 101, which is also attached to the sheath 103. This configuration of the sheath 103 provides support for the inflation member 105 and the ablation structure 101 irrespective of the positioning of the endoscope distal end 110. For example, as shown in FIG. 26, the endoscope distal end 110 can be positioned to provide a gap between the distal end 110 and a distal end of the sheath 103 where the ablation structure 101 and inflation member 105 are positioned. In contrast, as shown in FIGS. 27, 31 and 32, the endoscope distal end 110 can extend through and beyond the distal end of the sheath 103.

Figure 22:
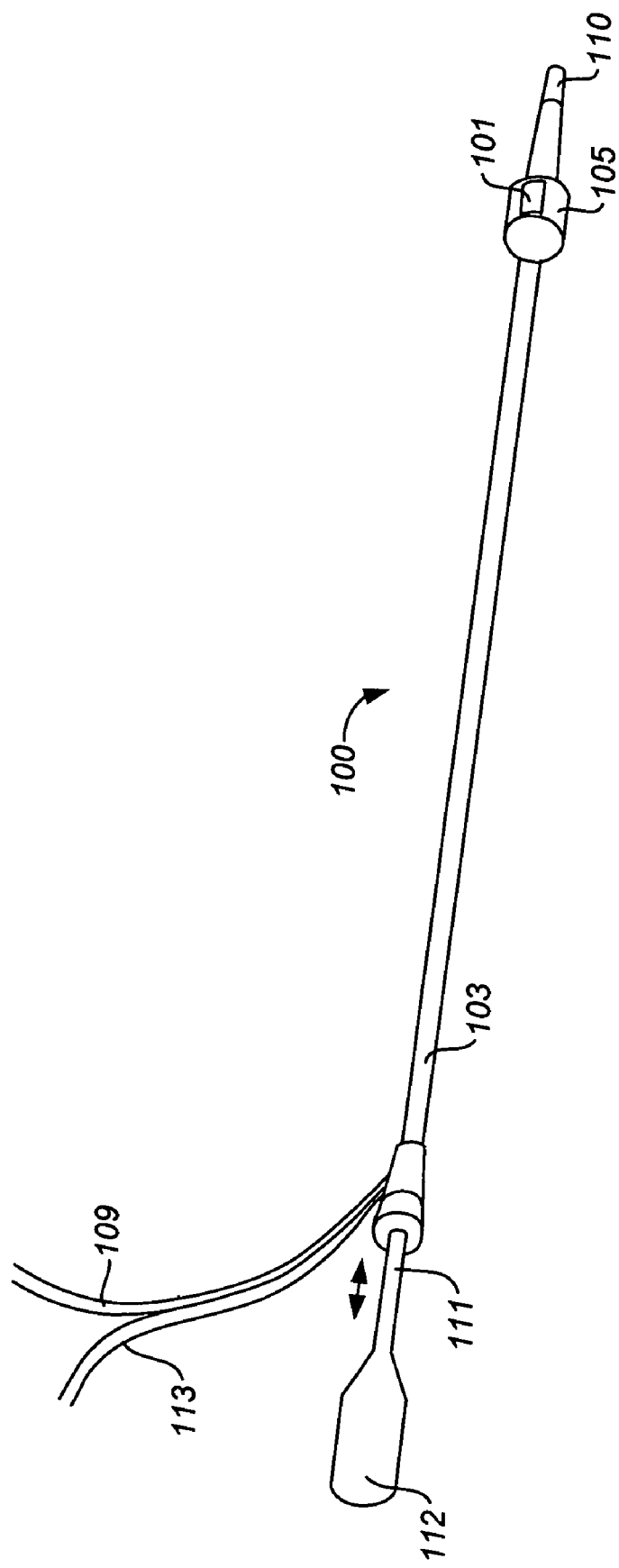
FIG. 22 is a view of the ablation device of the invention including an elongated sheath feature.

In another embodiment, as shown in FIG. 22, the sheath 103 can be elongated. FIG. 22 illustrates a sheath including electrical connections 109 and an inflation line 113. It is contemplated that the sheath 103 could include pneumatic and/or over extruded wires impregnated within the sheath 103. In use, the sheath 103 can be introduced first into an alimentary tract 1, wherein the sheath 103 serves as a catheter like guide for introduction of the endoscope 111 within the sheath 103. Alternatively, the endoscope 111 could be introduced first and thereby serve as a guidewire for the sheath 103 to be introduced over. FIG. 22 also shows attachment of an inflation member 105 to the sheath 103, in an arrangement wherein the ablation structure 101 is attached to the inflation member 105 opposite the sheath 103 attachment point.

Figure 23:
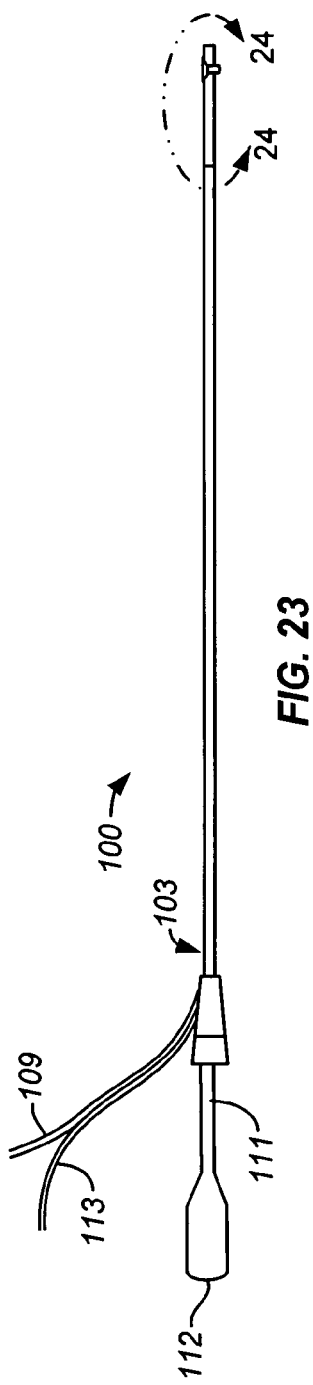
FIG. 23 is a view of the device wherein an elongated sheath feature is optically transmissive.
Figure 24:
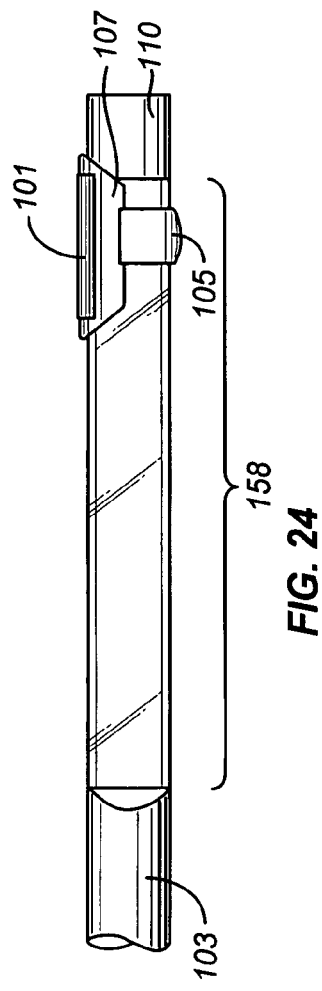
FIG. 24 is an enlarged view of the optically transmissive feature of the device shown in FIG. 23.
Figure 25:
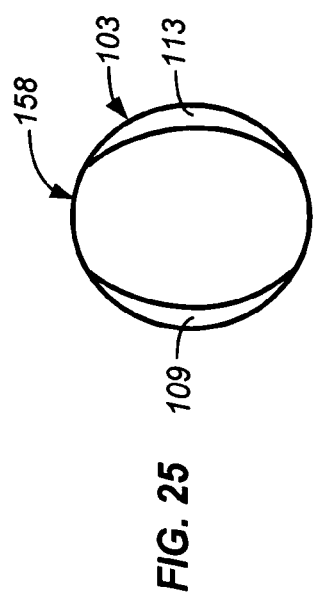
FIG. 25 is a cross sectional view of the optically transmissive sheath feature of the device shown in FIGS. 23 and 24.

In yet another embodiment, the sheath 103 includes an optically transmissive portion 158 adapted and configured to cooperate with a visual channel 161 of an endoscope 111. For example, the sheath 103 could be made of clear, translucent or transparent polymeric tubing including PVC, acrylic and Pebax® (polyether block amide). As shown in FIG. 19, one component of an endoscope 111 can be a visual channel 161 that provides visual imaging of a tissue surface 3 as imaged from the endoscope distal end 10. For example, the transmissive portion 158 could allow visualization of the wall of an esophagus 5 through the transmissive portion 158 of the sheath 103. As shown in FIG. 24 and in the cross-section view provided in FIG. 25, the sheaths 103 shown in FIGS. 23 and 24, include an optically transmissive portion 158 arranged and configured to provide viewing of tissue surfaces 3 through the wall of the sheath 103, with the aid of an internally disposed endoscope 111 having a visual channel 16 1. Also shown in cross-section in FIG. 25 are portions of the sheath 103 through which electrical connections 109 and an inflation line 113 can pass. It is contemplated that these features can be imbedded into the sheath 103 inner wall or attached to the sheath 103 inner wall. As shown in FIG. 26, the sheath 103 including a transmissive portion 158 can extend past the endoscope distal tip 110. Alternatively, as shown in FIGS. 23, 24 and 27, the endoscope distal end 10 can extend distally past the transmissive portion 158 of the sheath 103.

In another implementation, the transmissive portion 15 8 of the sheath 103 can be reinforced structurally with coil or braid elements incorporated therein to prevent ovalization and/or collapsing of the sheath 103, particularly while deflecting the ablation device 100

Figure 28:
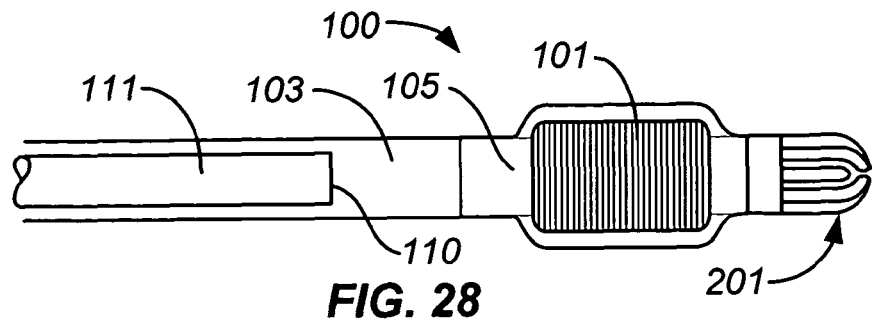
FIG. 28 is a view of the ablation device of the invention including a flexible tip feature.

As shown in FIG. 28, the sheath 103 can include a flexible tip 201 positioned on the sheath 103 distally to where the ablation structure 101 is attached to the sheath 103. The flexible curved surfaces of the flexible tip 201 can aid with accessing an alimentary tract 1.

Figure 29:
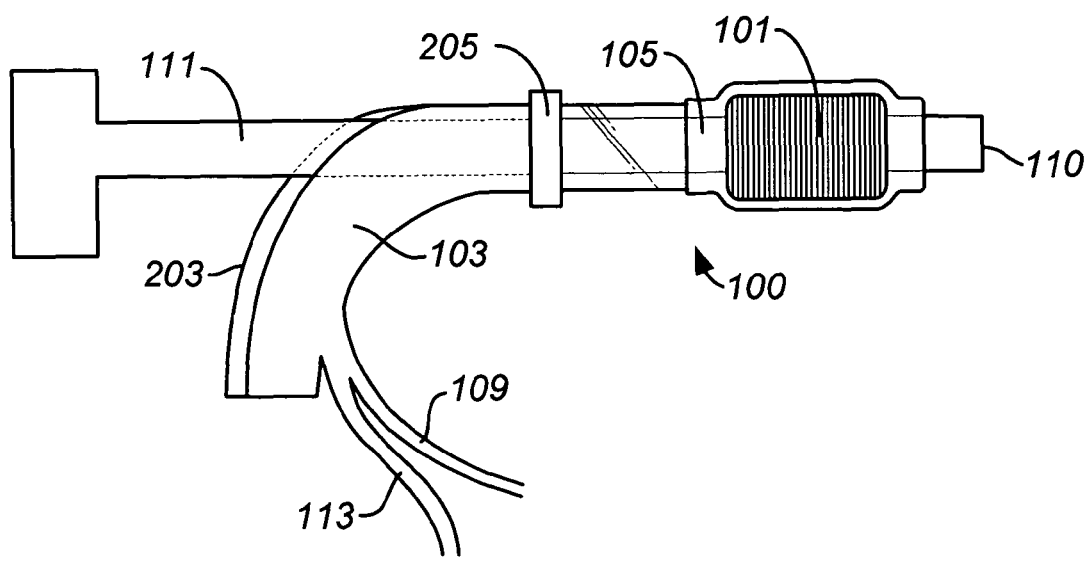
FIG. 29 is a view of the ablation device of the invention including a slit sheath feature.

In a further embodiment, the sheath 103 includes a slit 203 formed in a proximal portion of the sheath 103, the slit 203 being designed to open to admit an endoscope distal end 110 into the sheath 103. As shown in FIG. 29 the proximal portion of the sheath 103 can include a perforation region or slit 203. The slit 203 can extend partially of fully along the length of the sheath 103. The slit 203 enables the sheath 103 to be pulled back, or opened when, for example introducing an endoscope 111 into the sheath 103. In one implementation, as shown in FIG. 29, the sheath 103 additionally includes a locking collar 205 for locking the sheath 103 in a desired position in respect to the endoscope 111.

Figure 30A:
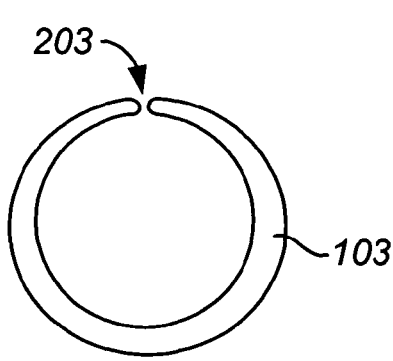
FIG. 30A is an end view of a slit sheath feature of the device wherein the sheath is in an unexpanded configuration.
Figure 30B:
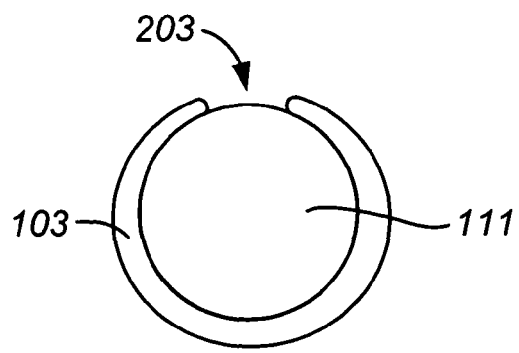
FIG. 30B is an end view of a slit sheath feature of the device and an endoscope wherein the sheath is in an expanded configuration.

As shown in FIGS. 30A and 30B, the distal portion of the sheath 103 can have a smaller outer diameter than a proximal portion of the sheath 103, the distal portion of the sheath 103 being adapted and configured to be expanded when an endoscope 111 is inserted into it (not shown). This embodiment can aid in accessing an endoscope 111 in a case where the sheath 103 is advanced first into an alimentary tract 1 such as the esophagus 5. Since the distal end of the sheath 103 is smaller in diameter, but includes a slit 203, the sheath 103 can accept a larger outside diameter endoscope 11 because when the endoscope 111 is advanced, the slit 203 of the sheath 103 allows for widening of the sheath 103.

As shown in FIGS. 31 and 32, the ablation device 100 can further include electrical connections 109 extending from the ablation structure 101 to a power source or supply 159 (not shown) and the sheath 103 can be adapted and configured to support the electrical connections 109.

In general, in another aspect, a method of ablating tissue in an alimentary tract includes advancing an ablation structure 101 into the alimentary tract while supporting the ablation structure 101 with an endoscope 111. The endoscope distal end 110 can be bent to move the ablation structure 101 into contact with a tissue surface followed by activation of the ablation structure 101 to ablate the tissue surface 3 (see e.g., FIG. 42). In a particular embodiment, the ablation structure 101 includes a plurality of electrodes and the activating step includes applying energy to the electrodes.

In general, in another aspect the coupling mechanism is designed to fit over an outside surface of an endoscope 111, to couple the ablation structure 101 with the endoscope 111, rather than being for example, a sheath (as discussed above), is adapted and configured to provide a certain freedom of movement to the ablation structure 101, including but not limited to flexing and/or rotating and/or pivoting with respect to the endoscope 111 when coupled to the endoscope 111. It is contemplated that the freedom of movement is about one, two or three axis thereby providing one, two or three degrees of freedom. Examples of suitable coupling mechanisms include but are not limited to a flex joint, pin joint, u joint, ball joint or any combination thereof. The following described coupling mechanism embodiments advantageously provide for a substantially uniform apposition force between a supporting endoscope 111 and an ablation structure 101 when localized at a target tissue surface 3.

Figure 42:
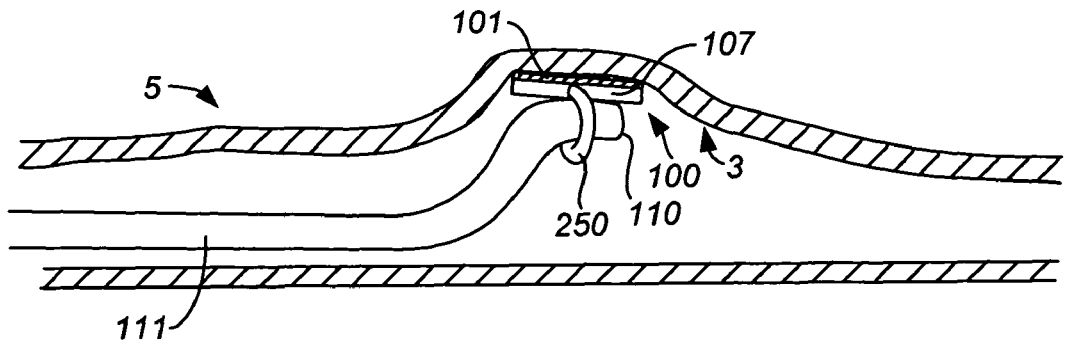
FIG. 42 is an illustration of the ablation device of the invention positioned within an esophagus showing a rotational feature.
Figure 44A:
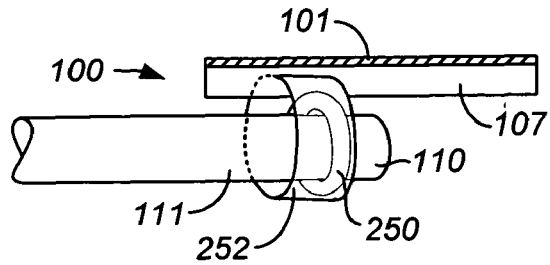
FIGS. 44A, 44B and 44C are views of the ablation device of the invention showing alternative rotational features.
Figure 44B:
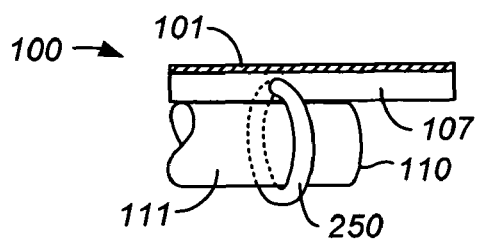

As shown in FIGS. 42, 43 and 44A and B, the coupling mechanism can be a ring 250 attached to the housing 107 and the endoscope 111, wherein the housing 107 is adapted and configured to flex, rotate or pivot about the ring 250. For example, as illustrated in FIG. 42 (see detailed view in FIG. 44B), where the ablation device 100 is coupled to a deflectable distal end 110 of an endoscope 111 by a ring 250, when the device 100 is deflected toward the tissue surface 3 of, for example, the esophagus 5, the housing 107 upon contact aligns the ablation structure 101 with the tissue surface 3 by flexing, rotating or pivoting about the ring 250 coupling. Advantageously, sufficient contact pressure provided by deflection of the distal end 110 of the endoscope 101 can produce a desired degree of contact between the ablation structure 101 and the tissue surface 3, irrespective of the precise alignment of the distal end 112 in respect to a plane of the tissue surface 3 to be treated. For the purposes of this disclosure, a "desired degree of contact" or "desired contact" between the ablation structure 101 and the tissue surface 3, includes complete or substantial contact between all or a portion of a predetermined target on the tissue surface 3 (e.g. abnormal mucosa 7) by all or a portion of the ablation structure 101.

As shown in FIG. 43, in a different yet related embodiment, where the deflection mechanism of the ablation device 100 is an inflatable member 105, a ring 250 coupling allows for flexing, rotating or pivoting of the housing 107 and ablation structure 101. As in the previous case, sufficient contact pressure provided through deflection, here by the inflatable member 105, can produce a desired degree of contact between the ablation structure 101 and the tissue surface 3. Again, advantageously, the desired contact can be achieved irrespective of the precise alignment of the deflected endoscope 111 distal end 110 in respect to a plane of the tissue surface 3 to be treated, because of the flexing, rotating or pivoting provided by the ring 250 coupling.

Figure 44C:
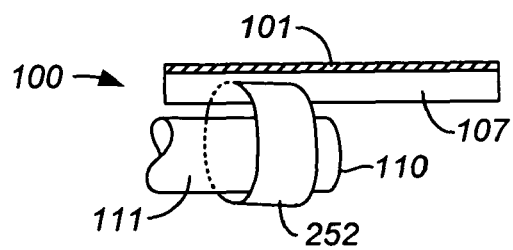

As shown in FIG. 44C, in a related embodiment, the coupling mechanism between the ablation device 100 and an endoscope 111 can be an elastic band 252, wherein the housing 107 of the device 100 is flexibly coupled to the elastic band 252. For example, as illustrated in FIG. 44C, where the ablation device 100 is coupled to a distal end 110 of an endoscope 111 by an elastic band 252, when the device 100 is deflected toward a tissue surface 3 of, for example, the esophagus 5 (not shown), alignment between the housing 107 and accordingly the ablation structure 101 and the tissue surface 3, can be achieved by flexing about the elastic band 252 coupling. Once more, advantageously, the desired contact can be achieved irrespective of the precise alignment of the deflected endoscope 111 distal end 110 in respect to a plane of the tissue surface 3 to be treated, because of the flexing provided by the elastic band 252 coupling.

As shown in FIG. 44A, in another related embodiment, the coupling mechanism between the ablation device 100 and an endoscope 111 can be a combination of a ring 250 and an elastic band 252, wherein the housing 107 of the device 100 is coupled to the elastic band 252. For example, as illustrated in FIG. 44A, where the ablation device 100 is coupled to a distal end 110 of an endoscope 111 by an elastic band 252, when the device 100 is deflected toward a tissue surface 3 of, for example, the esophagus 5 (not shown), alignment between the housing 107 and accordingly the ablation structure 101, and the tissue surface 3 by flexing, rotating or pivoting about the ring 250 and the elastic band 252 coupling can be achieved. Again, advantageously, the desired contact can be achieved irrespective of the precise alignment of the deflected endoscope 111 distal end 110 in respect to a plane of the tissue surface 3 to be treated, because of the flexing rotating or pivoting provided by the elastic band 252 coupling.

In another embodiment, the ablation device 100 additionally includes an alternative coupling mechanism between the ablation device 100 and an endoscope 111, that is arranged and configured to fit within a channel of an endoscope 111. The coupling mechanism can be an internal coupling mechanism 215 and can be configured and arranged to couple the ablation structure 101 within an internal working channel 211 of an endoscope 111 (see FIG. 36 and as discussed above)

As shown in FIGS. 33A, 33B, 34A, 34B, 35A and 35B, in one embodiment of such a coupling mechanism, the ablation structure 101 is adapted and configured to fit within the endoscope internal working channel 211. Additionally, as shown in FIGS. 33A, 33B, 34A, 34B, 35A and 35B, in a related embodiment, the deflection mechanism is also adapted and configured to fit within the endoscope internal working channel 211.

In each of the embodiments described above and shown in FIGS. 33A, 33B, 34A, 34B, 35A and 35B, after expansion of the inflatable member 105 or expandable member 209 and subsequent treatment of a target tissue 3, the coupling means can further serve as a means to draw, pull or retrieve the ablation structure 101 and deflection mechanism back into the endoscope internal working channel 211. Furthermore, in addition to providing coupling of the ablation structure 101 with the endoscope internal working channel 112, the coupling mechanism can include electrical connections 109 to provide energy to the ablation structure 101.

In a related embodiment, again wherein the ablation device 100 additionally includes a coupling mechanism adapted and configured to fit within a channel of an endoscope 111, the coupling mechanism can include a shape memory member and the deflection mechanism can include a bent portion of the shape memory member. As shown in FIGS. 36, 37 and 38, the coupling mechanism can be an internal coupling mechanism 215. As shown, the internal coupling mechanism 215 can be disposed within an endoscope internal working channel 211 and extend beyond the endoscope distal end 100. Additionally, the internal coupling mechanism 215 can be connected to a deflection mechanism that is a deflection member 150. The deflection member 150 can include a bent portion and can be connected to the housing 107. As shown in FIG. 37 and discussed above, the bent portion of the deflection member 150 can be disposed within the endoscope internal working channel 211, causing the ablation structure 101 to move into a non-deployed position. Upon advancing the internal coupling mechanism 215 toward the endoscope distal end 110, the shape memory nature of the deflection member 150 facilitates deployment of the ablation structure 101 to a position suitable for ablation.

In general, in one aspect, the ablation structure 101 of the ablation device 100 includes an optically transmissive portion 158 adapted and configured to cooperate with a visual channel of an endoscope 111. As shown in FIGS. 23, 24, 25, 26 and 27 and discussed above, the optically transmissive portion 158 can be a sheath 103 of the ablation device 100.

In one embodiment, the ablation structure 101 of the ablation device 100 is further adapted and configured to move from a first configuration to a second radially expanded configuration. As shown in FIGS. 14, 15, 16 and 17, the ablation structure 101 and housing 107 can be designed to reversibly move from a first less radially expanded configuration (see FIGS. 15 and 16) to a second radially expanded configuration useful for ablation. Foldable or deflectable configurations that provide for reversible radial expansion of the housing 107 and the ablation structure 101 can facilitate access to tissue surfaces because of reduced size. Additionally, foldable or deflectable configurations are helpful in regard to cleaning, introduction, retrieval, and repositioning of the device in the alimentary tract.

Figure 14:
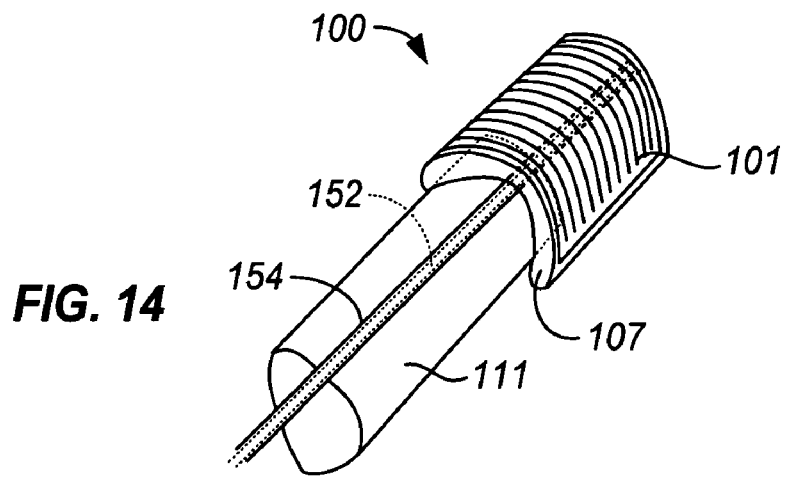
FIG. 14 is a view of the ablation device of the invention showing an alternative deflection member wherein the device is in an expanded configuration.
Figure 15:
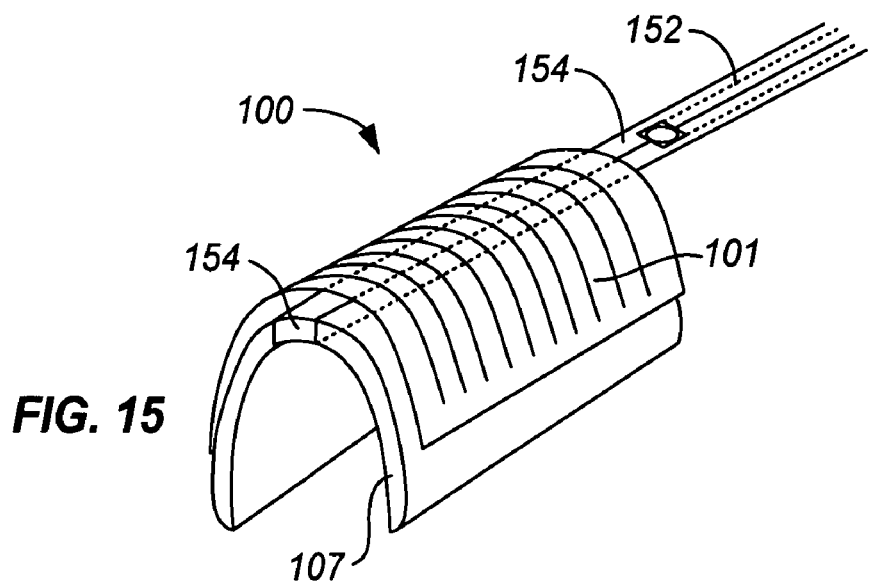
FIG. 15 is a view of device shown in FIG. 14 wherein the deflection member is in an unexpanded configuration.
Figure 16:
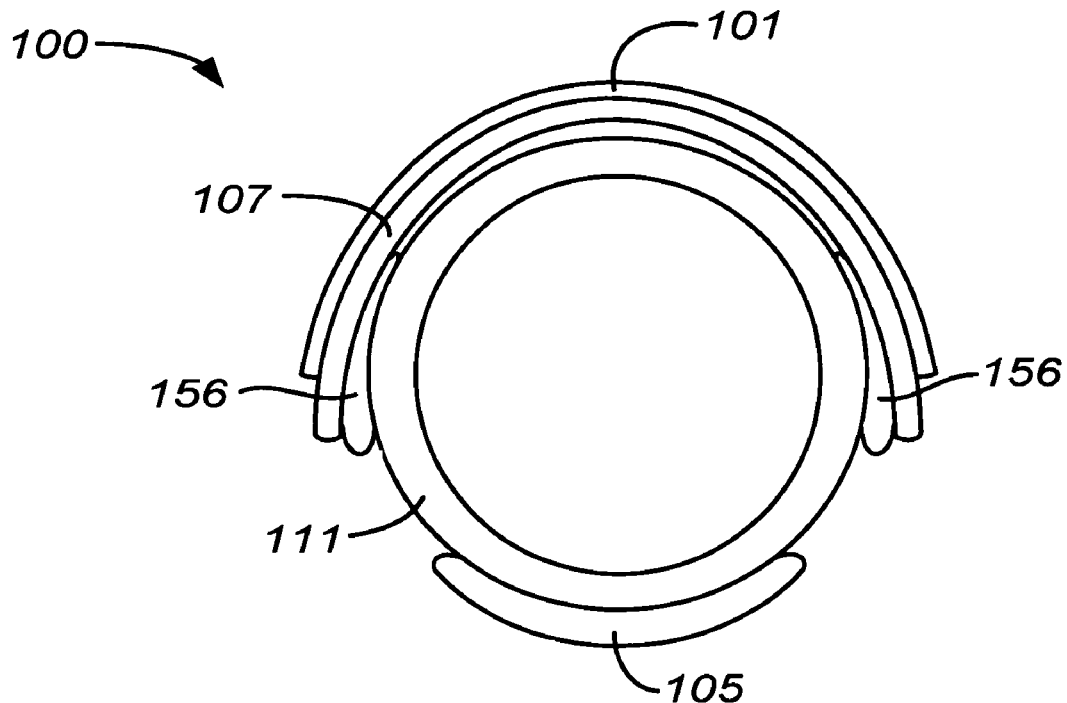
FIG. 16 is an end view of the device in an unexpanded configuration.

The ablation device 100 shown in FIGS. 14 and 15 includes an ablation structure actuator 152 arranged and configured to move the ablation structure 101 from the first configuration (see FIG. 15) to a second radially expanded configuration (see FIG. 16). As shown in FIGS. 14 and 15, the actuator 152 can be elongate and designed to work with a receiver 154 arranged and configured to receive the actuator 152. The actuator 152 can be a wire, rod or other suitable elongate structure. Alternatively, the actuator 152 can be a hydraulic actuation means with or without a balloon component. In a particular embodiment, the actuator 152 is a stiffening wire.

As illustrated in FIG. 15 before the actuator 152 is disposed within the portion of receiver 154 attached to the housing 107, both the housing 107 and the ablation structure 101 are in a first position having a first configuration. As illustrated in FIG. 14, after the actuator 152 is partially or fully introduced into the receiver 154, the housing 107 and the ablation structure 101 are consequently changed to a second radially expanded configuration relative to the first configuration. Introduction of the actuator 152 into the receiver 154 can force the portions of the housing 107 and ablation structure 101 flanking the receiver 154 to expand radially (see FIG. 14). In one embodiment, the housing 107 is heat set in a flexed first configuration suitable for positioning the ablation device 100 near a target tissue surface 3. After a target tissue surface 3 has been reached, the actuator 152 can be introduced into the receiver 154 to achieve the second radially expanded configuration which is useful for ablation of the tissue surface 3.

In a related alternative embodiment, the housing 107 and ablation structure 101 include an unconstrained shape that is radially expanded and includes one or more flex points to allow for collapsed or reduced radial expansion when positioned distally to the distal end 110 of an endoscope 111 and compressed by an elastomeric sheath 115 (not shown).

Figure 17:
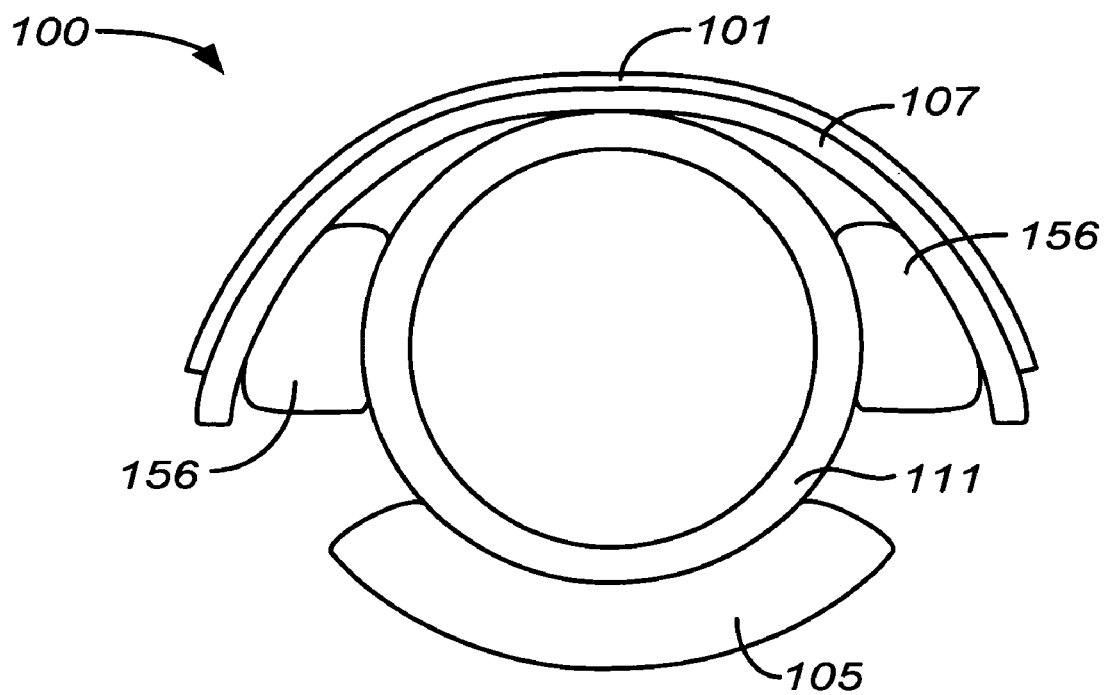
FIG. 17 is an end view of the device shown in FIG. 16 in an expanded configuration.

As shown in FIGS. 16 and 17, in another embodiment, the ablation structure 101 of the ablation device 100 is adapted and configured to move from a first configuration to a second radially expanded configuration wherein the ablation device 100 further includes an expandable member 156. As illustrated in FIG. 16, the expandable member 156 can be positioned between the housing 107 and the endoscope 111, where in unexpanded form, the ablation structure 101 is accordingly configured in a first configuration. Upon expansion of the expandable member 156, the ablation structure 101 configuration is changed to a second radially expanded configuration (see FIG. 17).

In one embodiment, the deflection mechanism of the ablation device 100 includes an inflatable inflation member 105. As shown in FIGS. 3, 16, 17, 22, 23, 24, 26, 27, 32, 33A-B, 41, 43, 45 and 46, and discussed above, the inflation member 105 can facilitate deflection of the device 100 in relation to a tissue surface 3.

In another embodiment, the deflection mechanism includes an expandable member 156 (see FIGS. 34B and 35B, discussed in detail above). As shown in FIG. 34B, the expandable member 209, can be an expandable stent, frame or cage device. As shown in FIG. 35B, the expandable member 209, can be an expanded series of connected hoops, that can be folded or rolled prior to expansion.

Figure 45C:
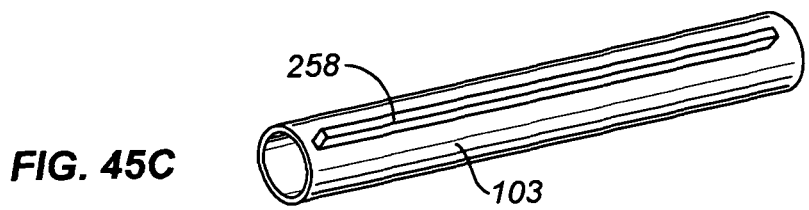
FIG. 45C is a view of a sheath feature of the device.

In another advantageous embodiment, the ablation device 100 further comprises a torque transmission member adapted and configured to transmit torque from a proximal end of the endoscope 111 to the ablation structure 101 to rotate the ablation structure 101 about a central axis of the endoscope 111. In a particular embodiment, the torque transmission member includes first and second interlocking members adapted to resist relative movement between the endoscope 111 and the ablation structure 101 about the central axis. As shown in FIGS. 45B, 45C and 46, in one embodiment the first interlocking member is a key 258 and the second interlocking member is a keyway 256. In one embodiment, the first interlocking member is attached to a sheath 103 surrounding the endoscope 111 and the second interlocking member is attached to a catheter 254 supporting the ablation structure 101. For example, as shown in FIGS. 45B, 45C and 46, the key 258 can be attached to a sheath 103 surrounding the endoscope 111 and the keyway 256 can be attached to a catheter 254 supporting the ablation structure 101. In a further related embodiment, the catheter 254 and sheath 103 are arranged and configured for relative movement along the central axis of the endoscope 111.

The sheath 103 can be, for example, an elastomeric sheath wherein the key 258 is attached to the outside of the sheath 103 substantially along a longitudinal axis of the sheath 103 (see FIG. 45C).

In use, this embodiment provides for a 1-to-1 torque transmission of the ablation device 100/endoscope 111 assembly when the endoscope proximal end 112 is manipulated, while also providing for positioning of the ablation structure 101 either proximal or distal to the endoscope distal end 110 in situ. Additionally, the sheath 103 can be pre-loaded into the catheter 254 or loaded separately In general, in one aspect, an ablation device 100 is provided including an ablation structure 101, and a coupling mechanism adapted to removably couple the ablation structure 101 to a distal end 110 of an endoscope 111 and to permit the ablation structure 101 to rotate and/or pivot with respect to the endoscope when coupled to the endoscope (see generally FIG. 21). Various related embodiments wherein, for example, the coupling mechanism comprises a ring 250 and the ablation structure 101 is adapted to rotate and/or pivot about the ring 250; wherein the coupling mechanism comprises an elastic band 252 adapted to flex to permit the ablation structure 101 to rotate and/or pivot; wherein the ablation device 100 further includes a deflection mechanism adapted and configured to move the ablation structure 101 toward a tissue surface 3; and, wherein such a deflection mechanism includes an inflatable member, have been set out in detail above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ablation device comprising:
   an endoscope having a central longitudinal axis;
   a support platform having a proximal end, a distal end and a central longitudinal axis extending between the proximal and the distal end;

an ablation structure having a proximal end, a distal end and an electrode surface, the ablation structure is supported by the support platform whereby the electrode surface faces away from the central longitudinal axis of the support platform; and a flexible coupling mechanism that encircles an exterior surface of the endoscope and attaches to the support platform between the proximal and the distal ends of the electrode surface.

2. The ablation device of claim 1 wherein the coupling mechanism to moveable relative to the endoscope.

3. An ablation device comprising:

an endoscope having a central longitudinal axis;

a support platform coupled to a distal portion of the endoscope, the support platform having a central longitudinal axis;

an ablation structure supported on a surface of the support platform that faces away from the central longitudinal axis of the endoscope; and a coupling mechanism connected between the proximal and distal ends of the support platform and between the proximal and distal ends of the ablation structure while allowing pivoting movement between the central longitudinal axis of the support platform and the central longitudinal axis of the endoscope.

4. The device of claim 3 wherein the coupling mechanism comprises a ring.

5. The device of claim 3 wherein the coupling mechanism comprises an elastic band.

6. The device of claim 3 further comprising a deflection mechanism attached to the distal end of the endoscope radially opposite the support platform.

7. The device of claim 6 wherein the deflection mechanism comprises an expandable member.

8. The ablation device of claim 7 wherein the expandable member is a balloon.

9. The ablation device of claim 3 wherein the coupling mechanism is adapted to removably couple the ablation structure to the endoscope.

10. The device of claim 3 wherein the coupling mechanism is adapted to permit the ablation structure to flex with respect to the endoscope when coupled to the endoscope.

11. The device of claim 3 wherein the coupling mechanism includes a combination of a ring and an elastic band.

12. The ablation device of claim 3 wherein the coupling mechanism is positioned proximal to a distal end of the endoscope.

13. The ablation device of claim 3 wherein a portion of the support platform is disposed proximal to the coupling mechanism.

14. The ablation device of claim 13 wherein a portion of the support platform is disposed distal to the coupling mechanism.

15. The ablation device of claim 3 wherein the support platform is disposed adjacent to the coupling mechanism.

16. The ablation device of claim 3 wherein the longitudinal axis of the support platform is substantially coplanar with the central longitudinal axis of the endoscope.

17. The ablation device of claim 3 wherein the coupling mechanism is configured to be pivotable such that the longitudinal axis of the endoscope and the longitudinal axis of the support platform may be disposed in a parallel or non-parallel relationship.

18. The ablation device of claim 3 wherein the coupling mechanism is configured to be pivotable such that upon pivoting, one portion of the support platform is disposed closer to the endoscope and another portion of the support platform is disposed further from the endoscope.

19. An ablation device comprising:

an endoscope having a central longitudinal axis;

a support platform coupled to a distal portion of the endoscope, the support platform having a longitudinal axis;

an ablation structure supported on a surface of the support platform that faces away from the central longitudinal axis of the endoscope; and a coupling mechanism connected between the proximal and distal ends of the support platform and between the proximal and distal ends of the ablation structure while allowing pivoting movement of the support platform about an axis transverse to the central longitudinal axis of the endoscope.

20. The device of claim 3, 1 or 19 wherein the ablation structure comprises a plurality of electrodes.

21. The ablation device of claim 20 wherein the spacing between adjacent electrodes in the plurality of electrodes is from 0.1 mm to 20 mm.

22. The device of claim 3, 1 or 19 wherein the coupling mechanism includes any of a flex joint, a pin joint, a U-joint, a ball joint or any combination thereof.

23. The ablation device of claim 3, 1 or 19 wherein the coupling mechanism is configured to be pivotable in response to deflection of the ablation structure against a surface.

24. The ablation device of claim 3, 1 or 19 wherein the ablation structure achieves thermal damage through heating tissue.

25. The ablation device of claim 3, 1 or 19 wherein the ablation structure achieves thermal damage through cooling tissue.

26. The ablation device of claim 3, 1 or 19, the ablation structure further comprising: a bipolar array of electrodes.

27. The ablation device of claim 3, 1 or 19 wherein the support platform is between the endoscope and the ablation structure.

28. The ablation device of claim 3, 1 or 19 wherein the ablation structure has an area in the range from 0.5 cm$^2$ to 9.0 cm$^2$.

* * * * *